United States Patent [19]

Tsutsui

[11] Patent Number: 4,716,220
[45] Date of Patent: Dec. 29, 1987

[54] DISAZO COMPOUNDS WITH XANTHONE NUCLEUS FOR ELECTROPHOTOGRAPHY

[75] Inventor: Kyoji Tsutsui, Mishima, Japan

[73] Assignee: Ricoh Co., Ltd., Tokyo, Japan

[21] Appl. No.: 753,281

[22] Filed: Jul. 9, 1985

Related U.S. Application Data

[62] Division of Ser. No. 597,991, Apr. 9, 1984, Pat. No. 4,540,643.

[30] Foreign Application Priority Data

Apr. 26, 1983 [JP] Japan .................................. 58-73177
Apr. 28, 1983 [JP] Japan .................................. 58-75586

[51] Int. Cl.⁴ ........................ C09B 35/03; G03G 5/06; G03G 5/14
[52] U.S. Cl. .................................. 534/738; 534/560; 534/565; 534/581; 534/757; 534/761
[58] Field of Search ................................ 534/761, 757

[56] References Cited

U.S. PATENT DOCUMENTS 1,624,944  4/1927  Gleitenberg ..................... 534/761 X
4,390,611  6/1983  Ishikawa et al. ................. 534/761 X

FOREIGN PATENT DOCUMENTS 57-102643  6/1982  Japan .................................. 534/761
58-5364    1/1983  Japan .................................. 534/761

Primary Examiner—Floyd D. Higel
Attorney, Agent, or Firm—Flynn, Thiel, Boutell & Tanis

[57] ABSTRACT

The present invention provides a tetrazoneum salt compound represented by the general formula (I):

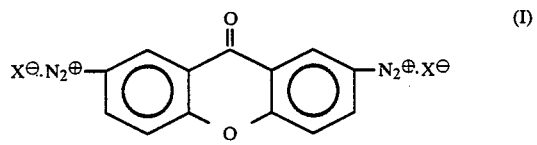

(wherein, X stands for an anion functional group); a disazo compound represented by the general formula (II):

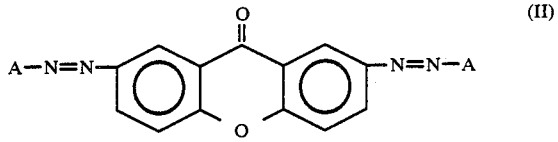

wherein, A stands for (Abstract continued on next page.)

-continued

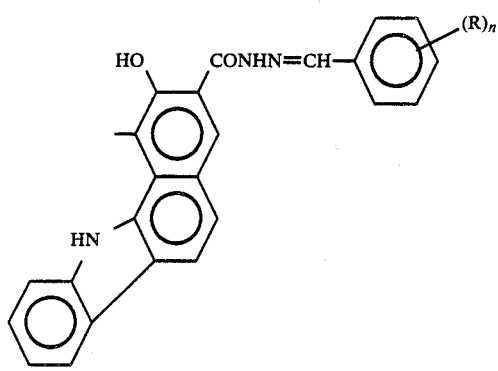

(wherein, R stands for an alkyl group, an alkoxy group, a nitro group, halogen, a cyano group or a halomethyl group, n stands for an integer of 0, 1, 2 or 3, and in case n is an integer of 2 or 3 R may be the same or different.); a method for the production thereof, and electrophotographic elements using the same or like disazo compounds as the charge carrier generating materials.

15 Claims, 7 Drawing Figures

DISAZO COMPOUND NO. 1

DISAZO COMPOUNDS WITH XANTHONE NUCLEUS FOR ELECTROPHOTOGRAPHY

This is a division of application Ser. No. 597,991, filed Apr. 9, 1984, now U.S. Pat. No. 4,540,643.

BACKGROUND OF THE INVENTION (a) Field of the invention

The present invention relates to novel tetrazonium salt compounds, novel disazo compounds and the method of producing said compounds, and electrophotographic elements containing these disazo compounds and the like, in particular relates to electrophotographic elements provided with photosensitive layers containing said disazo compounds as materials that generate charge carriers when exposed to light (which will be called charge carrier generating materials hereinafter), preferably multilayer type electrophotographic elements comprising layers containing said charge carrier generating materials (which will be called charge carrier generating layers hereinafter) and layers containing materials which receive the charge carriers generated in said charge carrier generating layers and transfer them (which will be called charge transfer materials hereinafter) respectively.

(b) Description of the prior art

As the conventional electrophotographic elements, there can be enumerated inorganic and organic ones. The inorganic system electrophotographic elements include those using selenium and its alloys and those prepared by dispersing dye-sensitized zinc oxide in binder resins, while as the organic system electrophotographic elements, there can be typically enumerated those using a charge transfer complex of 2,4,7-trinitro-9-fluorenone (which will be called TNF hereinafter) and poly-N-vinylcarbazole (which will be called PVK) and the like. But, it is also fact that these electrophotographic elements have various advantages, while having various disadvantages. For instance, the selenium electrophotographic elements which have presently been used universally are defective in that the manufacturing conditions are strict, the manufacturing cost is expensive, it is difficult to process them into belt-like form due to the absence of flexibility, attention must be paid in handling them because they are highly sensitive to heat and mechanical impact. Referring to zinc oxide elements, the manufacturing cost is low because they can be manufactured by applying cheap zinc oxides onto substrates, but said electrophotographic elements are defective mechanically in that they are generally inferior in sensitivity, surface-smoothness, solidity, tensile strength, friction resistance and the like and involve various problems to be solved in respect of durability and the like as the elements used repeatedly in copying plain papers. The electrophotographic elements using charge transfer complexes of TNF and PVK are so inferior in sensitivity that they are not suitable for the elements for use in high-speed copying machines.

Of late years, a wide range of studies have been carried out in order to eliminate the shortcomings inherent in these electrophotographic elements. In particular, various organic electrophotographic elements have been proposed for that purpose. Among them, multilayer type elements are attracting public attention as electrophotographic elements for use in plain paper copying machines due to their high sensitivity and stable chargeability as compared with usual organic electrophotographic elements, said multilayer type electrophotographic element comprising an electrically conductive substrate, a charge carrier generating layer formed by depositing on said electrically conductive substrate a thin film of organic pigment; and a charge transfer layer formed on said charge carrier generating layer and consisting essentially of a charge transfer material. And, some of them are put to practical use.

As the conventional multilayer type electrophotographic elements of this sort, there are known:

(1) the multilayer type electrophotographic element using, as the charge carrier generating layer, a thin layer formed by vacuum-vapordepositing a perylene derivative and incorporating an oxadiazole derivative in the charge transfer layer (which see U.S. Pat. No. 3871882), (2) the multilayer type electrophotographic element using, as the charge carrier generating layer, a thin layer formed by coating on organic amine solution of Chloro Dian Blue and incorporating a hydrazone compound in the charge transfer layer (which see Japanese Patent Publication No. 42380/1980), (3) the multilayer type electrophotographic element using, as the charge carrier generating layer, a thin layer formed by coating an organic solvent dispersion of distyrylbenzene type disazo compound and incorporating a hydrazone compound in the charge transfer layer (which see Japanese Laid Open Patent Application No. 84943/1980).

However, the fact is that even in the multilayer type electrophotographic elements of this sort, the conventional ones have a number of advantages as well as various disadvantages.

That is, the electrophotographic element using the perylene and oxadiazole derivatives disclosed in the preceding (1) is disadvantageous in that the cost of production is raised because the charge carrier generating layer is formed by vacuum vapor-deposition.

The electrophotographic element using the Chloro Dian Blue and hydrazone compound disclosed in the preceding (2) involves disadvantages in the preparation because there is necessity of using a hard-to-handle organic amine (for instance, ethylene-diamine) as a coating solvent for the formation of the charge carrier generating layer. Further, this electrophotographic element is inferior in the reproductivity of red images from the original because its visible light wavelengths cover the range of about 450–660 nm. Due to this, it is necessary to employ a filter to cut a red light when this element is actually set in the copying machine, thereby exerting an unprofitable influence upon the copying machine design.

The electrophotographic element using the distyrylbenzene type disazo compound and hydrazone compound disclosed in the preceding (3) is very profitable in the preparation because the charge carrier generating layer can be formed readily by coating a dispersion of disazo compound, but is defective, like the electrophotographic element disclosed in the preceding (2), in that the reproductivity of red images from the original is inferior because its sensitive light wavelengths cover the range of about 450–700 nm.

As the disazo compounds used in the multilayer type electrophotographic elements, there are also known, for instance, the benzidine type disazo compound disclosed in Japanese Laid Open Patent Application Nos. 37543/1972 and 55643/1977, the stilbene type disazo compound disclosed in Japanese Laid Open Patent Application No. 8832/1977. However, the multilayer type electrophotographic elements using these conventional disazo compounds were generally low in sensitivity and deteriorated in the reproductivity of red images from the original because their sensitive light wavelengths cover the range of about 450–700 nm. Accordingly, these electrophotographic elements were unprofitable in the copying machine design as stated previously, because these elements had to employ a filter to cut a red light when they are actually set in the copying machines.

SUMMARY OF THE INVENTION

It is an object of the present invention to provide a novel tetrazonium salt compound which is capable of producing a variety of disazo compounds used effectively in electrophotographic elements, in particular the above mentioned multilayer type electrophotographic elements.

It is another object of the present invention to provide a novel disazo compound used effectively in electrophotographic elements, in particular the above mentioned multilayer type elements. The multilayer type electrophotographic element using the disazo compound according to the present invention is high in sensitivity as compared with the electrophotographic elements using the conventional disazo compounds, and is also superior in the reproductivity of red images from the original as compared with said conventional electrophotographic elements because the sensitivity light wavelength range of the present electrophotographic element is localized only to the short wave length side of the visible light wavelength range (about 450–600 nm).

It is a further object of the present invention is to provide a method of making the above mentioned disazo compound.

It is still a further object of the present invention to provide an electrophotographic element which can be produced readily, is high in sensitivity and is superior in the reproductivity of red images from the original because its sensible light wavelengths are localized in the short wavelength range.

That is, the present invention is primarily directed towards a novel tetrazonium salt compound represented by the following general formula (I):

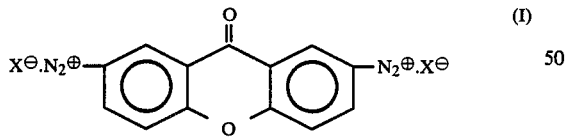

(wherein, X stands for an anion functional group.)

The tetrazonium salt compound represented by the formula (I) is a useful intermediate of the novel disazo compound according to the present invention, which is coupled with proper couplers to synthesize a variety of disazo compounds having xanthone skeletons and azo groups in the 2- and 7-positions thereof. And, this disazo compound is expected to be used as a photo-conductive material in the electrophotographic element, in particular a charge carrier generating material.

As the typical anion functional groups in the tetrazonium salt compound represented by the general formula (I), there can be enumerated: $Cl^\ominus$, $Br^\ominus$, $I^\ominus$, $BF_4^\ominus$, $PF_5^\ominus$,

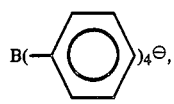

$ClO_4^\ominus$, $SO_4^{2\ominus}$,

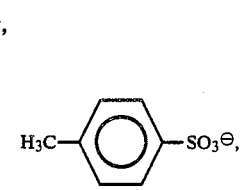

$AsF_6^\ominus$, $SbF_6^\ominus$, preferably $BF_4^\ominus$.

The present invention is secondarily directed towards a novel disazo compound represented by the general formula (II):

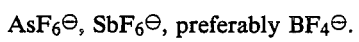

[wherein, A stands for

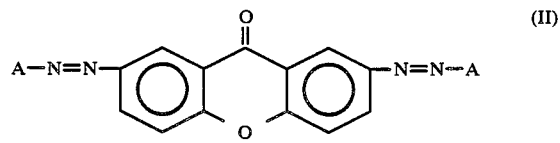

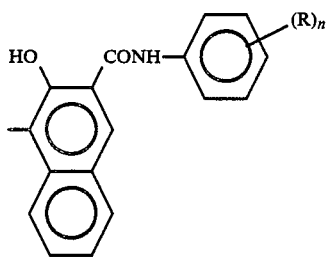

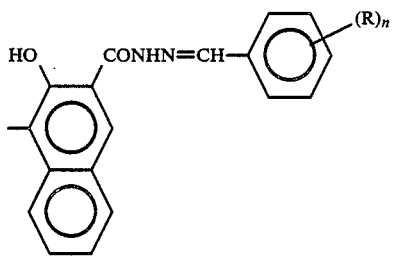

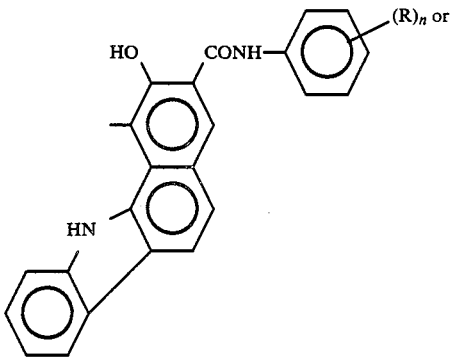

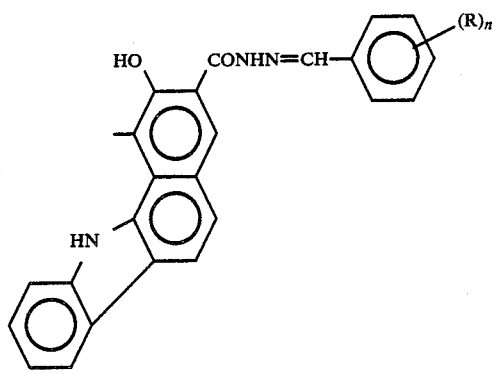

(R stands for an alkyl group such as methyl, ethyl, propyl butyl or the like, an alkoxy group such as methoxy, ethoxy, propoxy, butoxy or the like, a nitro group, halogen, a cyano group or a halomethyl group; n stands for an integer of 0, 1, 2 or 3; and in case n is an integer of 2 or 3, R may be the same or different group.)]

The disazo compound represented by the formula (II) of the present invention, as stated above, is useful as the charge carrier generating material especially in the multilayer type electrophotographic element, and additionally is useful as the charge carrier generating material in the electrophotographic element having the monolayer type photosensitive layer which comprises dispersing the charge carrier generating material and the charge transfer material in a resin and is also useful as the photoconductive material in the electrophotographic element having the photosensitive layer which comprises dispersing the photoconductive material in the resin.

The disazo compounds represented by the general formula (II) are all colored crystals. Next, the typical examples of these disazo compounds will be shown.

| Compound No. | Structural Formula |
|---|---|
| 1 | 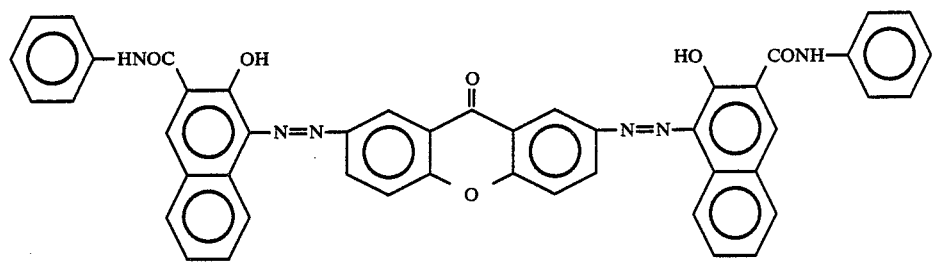 |
| 2 | 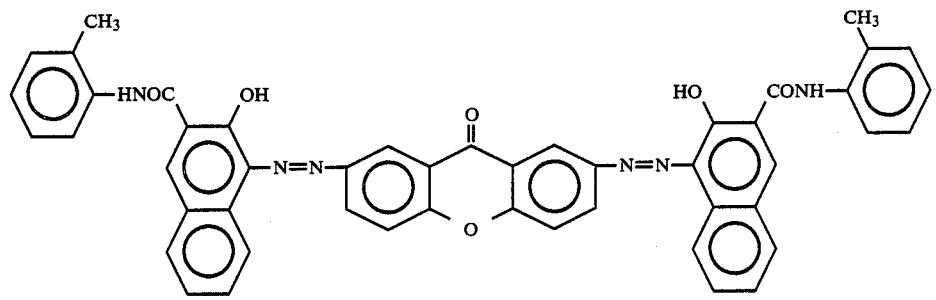 |
| 3 | 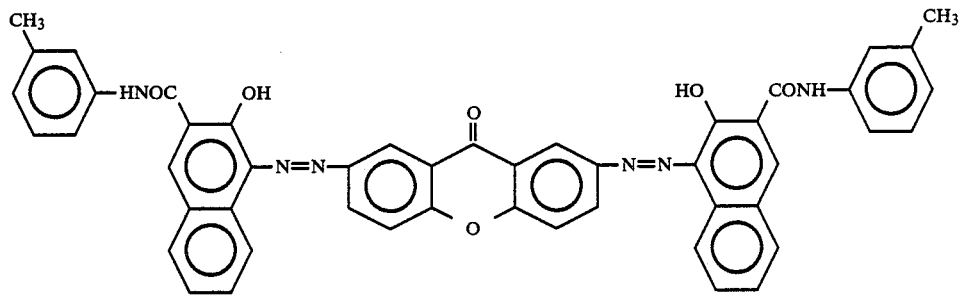 |

-continued
| Compound No. | Structural Formula |
|---|---|
| 4 | 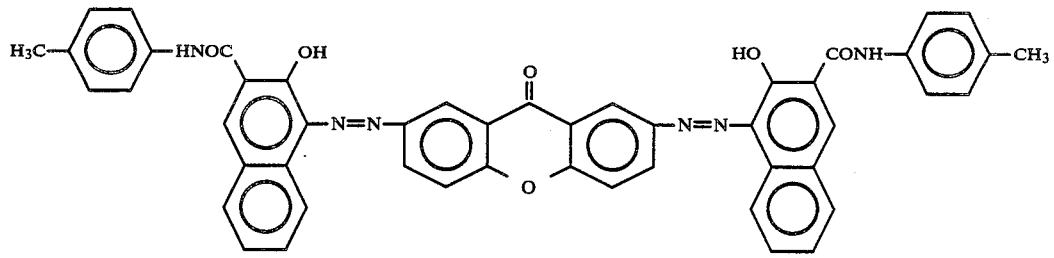 |
| 8 | 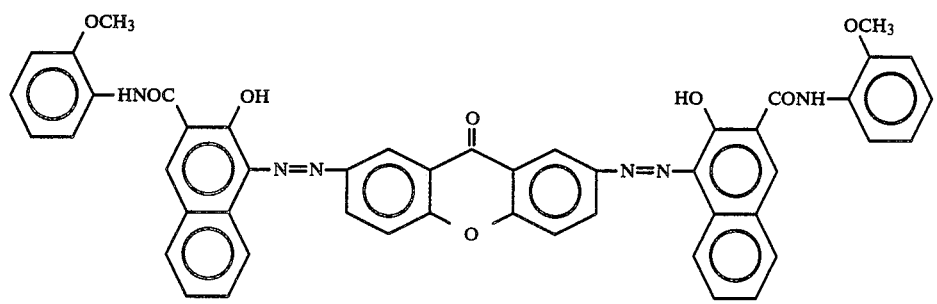 |
| 9 | 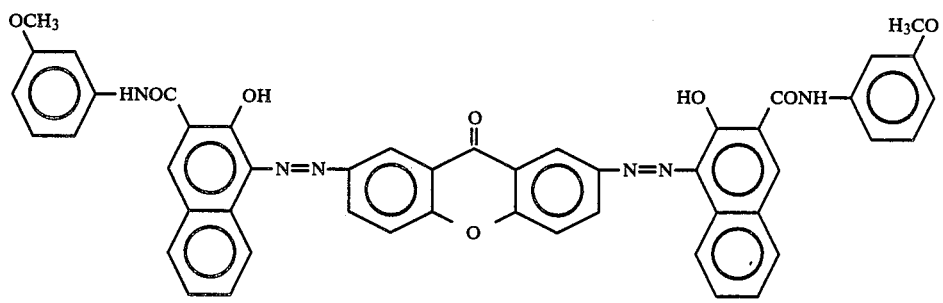 |
| 10 | 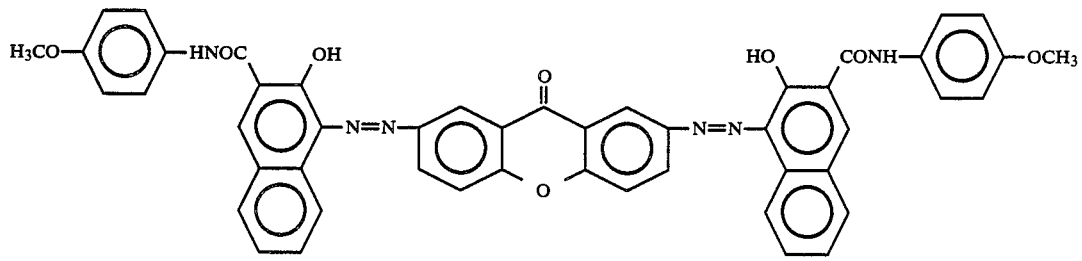 |
| 5 | 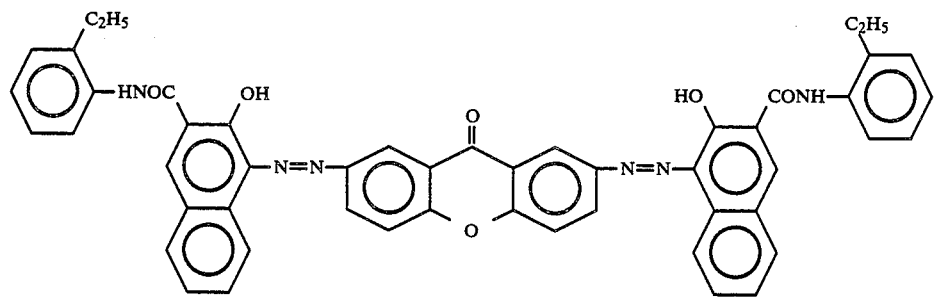 |

-continued

| Compound No. | Structural Formula |
|---|---|
| 7 | |
| 11 | |
| 12 | |
| 13 | |
| 14 | |

-continued

| Compound No. | Structural Formula |
|---|---|
| 15 | |
| 16 | |
| 17 | |
| 18 | |
| 19 | |

-continued
| Compound No. | Structural Formula |
|---|---|
| 20 | 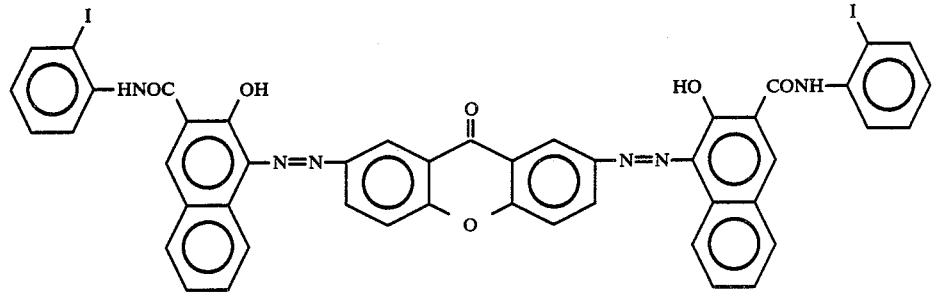 |
| 21 | 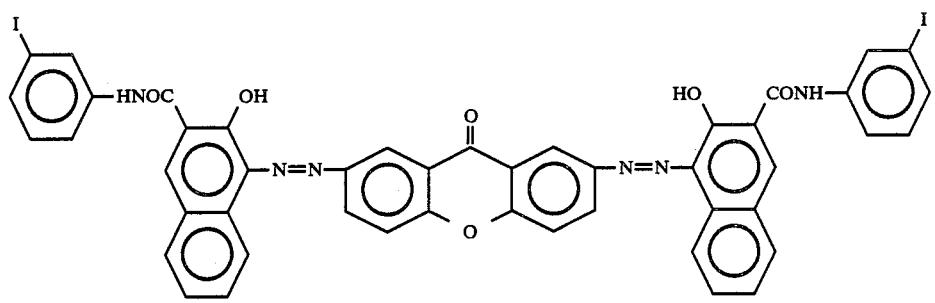 |
| 23 | 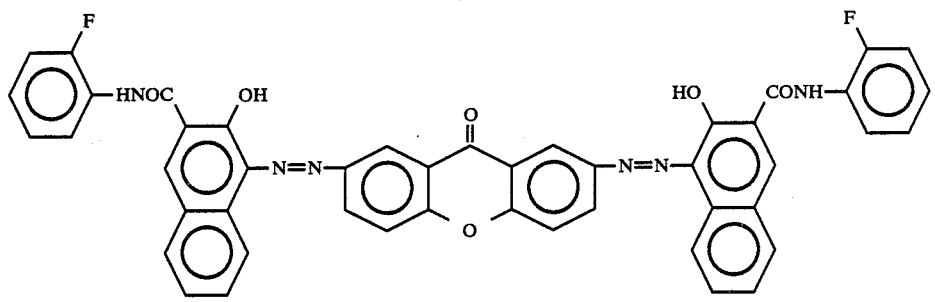 |
| 25 | 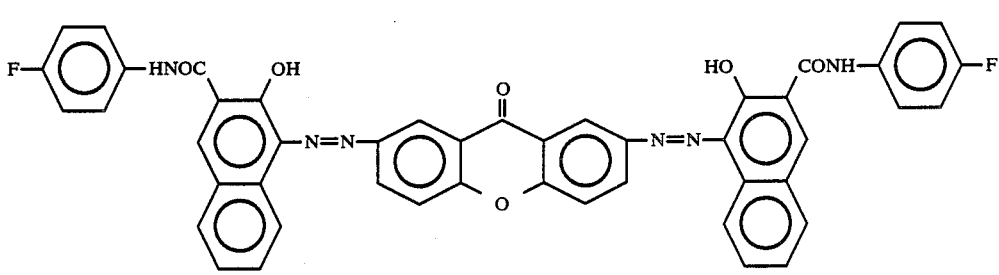 |
| 29 | 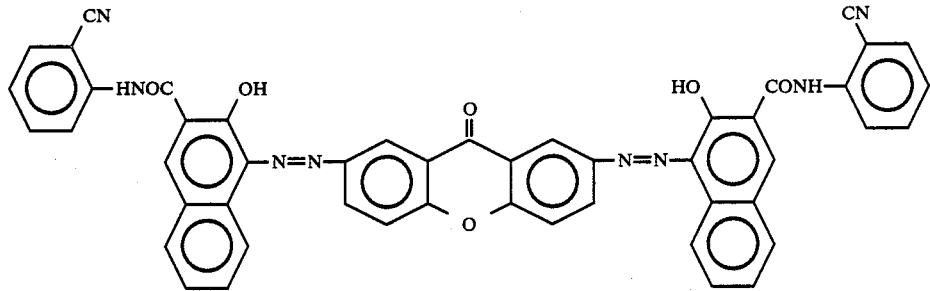 |

-continued

| Compound No. | Structural Formula |
|---|---|
| 26 | |
| 32 | |
| 33 | |
| 34 | |
| 44 | |

-continued

| Compound No. | Structural Formula |
|---|---|
| 41 | |
| 45 | |
| 77 | |
| 58 | |
| 90 | |

-continued
| Compound No. | Structural Formula |
|---|---|
| 84 | 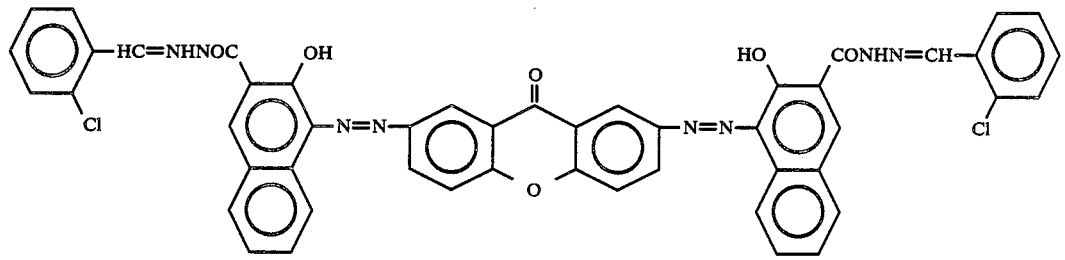 |
| 163 | 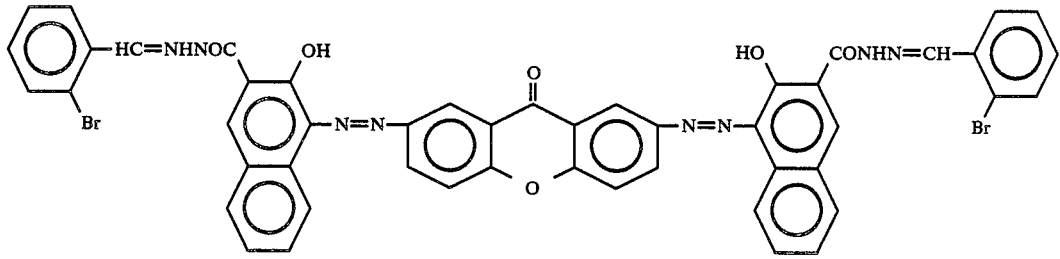 |
| 61 | 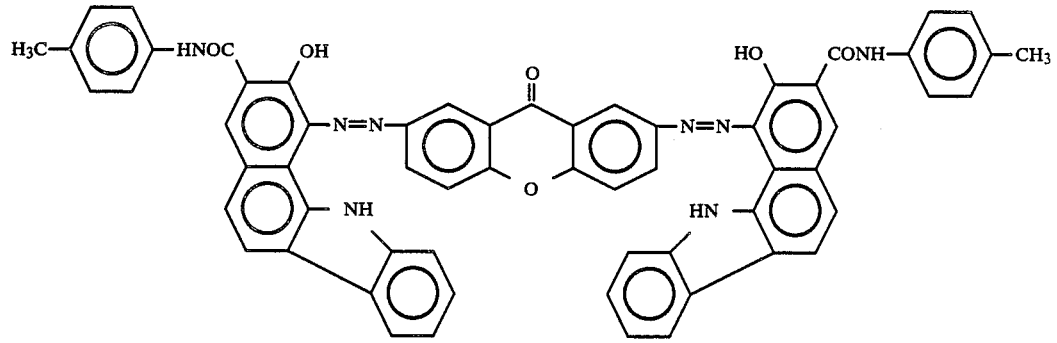 |
| 65 | 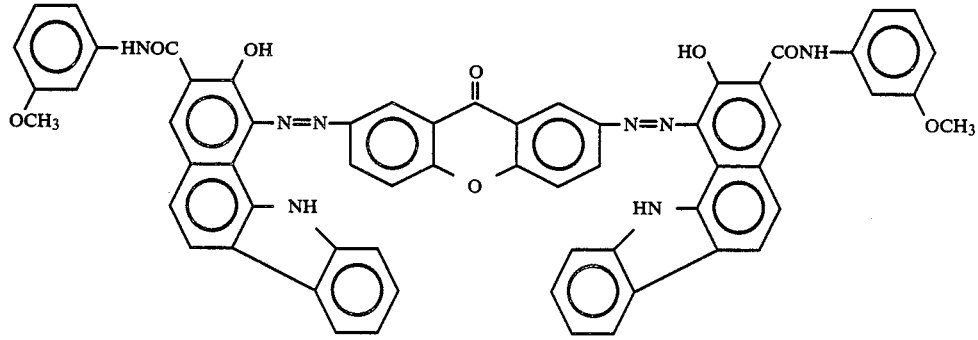 |
| 86 | 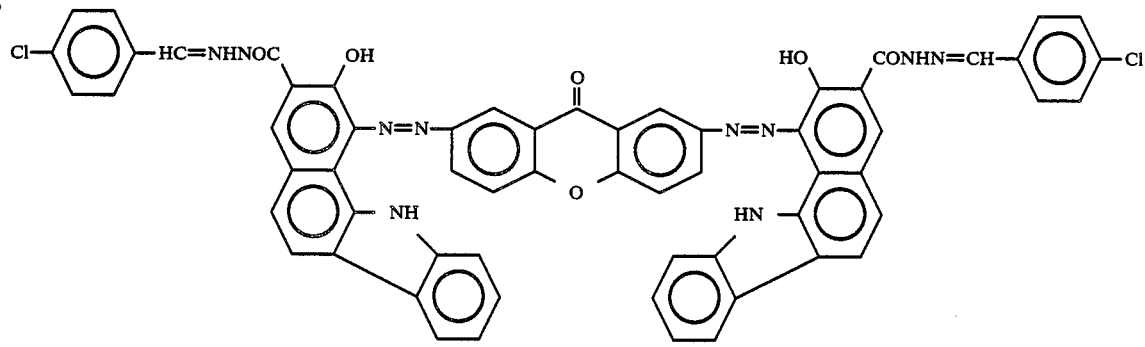 |

| Compound No. | Structural Formula |
|---|---|
| 164 | 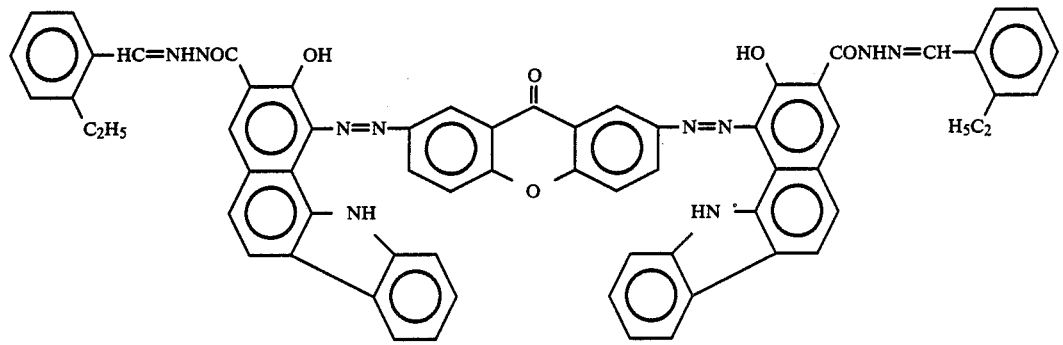 |

The present invention is further directed towards a process for manufacturing a novel disazo compound represented by the general formula (II):

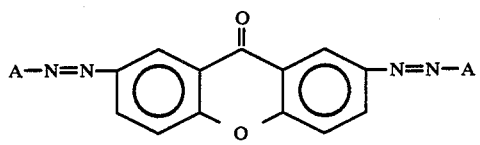 (II)

(wherein A is the same defined above) which comprises the steps of diazotating a diamino compound represented by the formula (III):

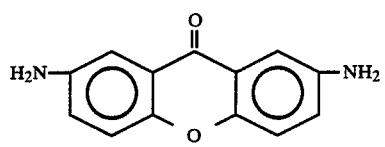 (III)

into tetrazonium salt represented by the general formula (I):

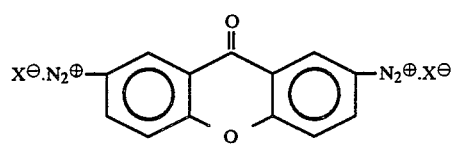 (I)

(wherein X is the same defined above), and then reacting this tetrazonium salt with a compound (which will be called a coupler hereinafter) represented by the general formula (IV), (V), (VI) or (VII):

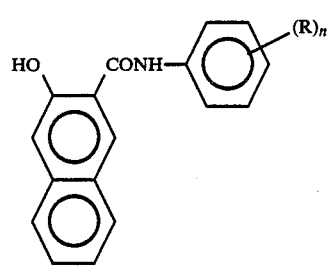 (IV)

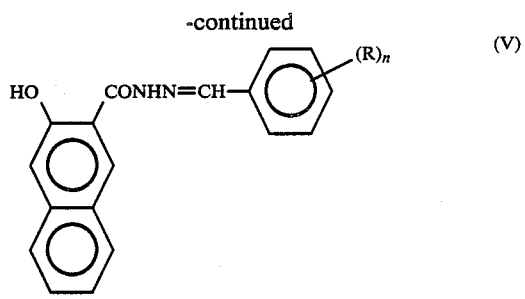 (V)

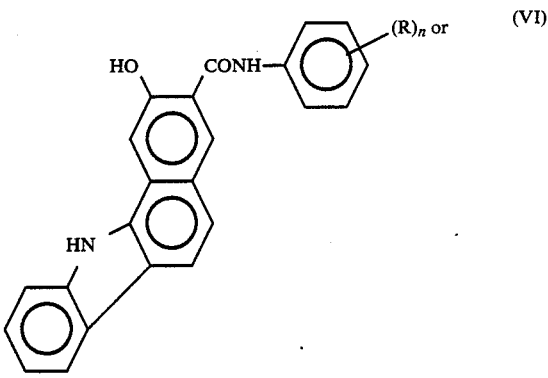 (VI)

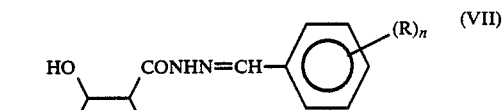 (VII)

(wherein R and n are the same defined above).

The tetrazonium salt represented by the general formula (I) of the present invention can be obtained by reducing, for instance, 2,7-dinitroxanthone into the diamino compound represented by the formula (III), and then diazotating it. In more detail, the process for manufacturing 2,7-dinitroxanthone and 2,7-diaminoxanthone is as described below. For instance, as described in A. A. Goldbery and H. A. Walker, Journal of Chemical Society, 1953, 1348 (1953), 2,7-dinitroxanthone can be obtained by nitrating xanthone in fuming nitric acid, and 2,7-diaminoxanthone can be obtained by reducing 2,7-dinitroxanthone in hydrochloric acid by using a reducing agent such as stannous chloride. The reducing reaction is carried out at a temperature of 95°–100° C. and completed in about 3 hours.

Diazotation of 2,7-diaminoxanthone (III) is carried out by adding sodium nitrite thereto in an inorganic acid such, for instance, as hydrochloric acid or sulfuric acid at a temperature of −10° C. to 20° C. This diazotation reaction is completed in about 30 minutes to 3 hours. Further, by adding for instance borofluoric acid or an aqueous sodium borofluorate solution to this diazotation reaction solution there can be obtained tetrazonium salt.

The preparation of the disazo compound represented by said general formula (II) can also be effected by the action of said diazotation reaction solution per se on a coupler, and further can be effected by the steps of adding for instance borofluoric acid or an aqueous sodium borofluorate solution to the diazotation reaction solution, causing precipitation of tetrazonium salt, isolating the tetrazonium salt, and then making it react with a coupler. Practically, this reaction is carried out by preparing a mixed solution of tetrazonium salt, coupler and an organic solvent such as N,N-dimethylformamide (DMF), dimethyl sulfoxide (DMSO) or the like, and dropping an aqueous alkali solution, for instance, such as an aqueous sodium acetate solution therein at a temperature of about −10° C. to 40° C. This reaction completes in about 5 minutes to 3 hours. After completion of said reaction, separated crystals are filtered and refined by using a proper way (for instance, washing with water or/and organic solvent, recrystallization or the like). Thus, the preparation of said disazo compound is completed.

The present invention is still further directed towards a multilayer type electrophotographic element comprising an electrically conductive substrate and a photosensitive layer, formed on the substrate, containing a disazo compound represented by the following general formula (VIII) (which will be called sometimes "disazo pigment" hereinafter) as a charge carrier generating material:

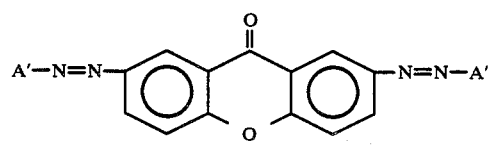
(VIII)

(wherein, A' stands for a coupler group.)

The coupler used in the present invention includes for instance phenolic hydroxyl group-containing compounds such as phenols, naphthols and the like; amino group-containing aromatic amino compounds; or amino group and phenolic hydroxyl group-containing aminonaphthols; aliphatic or aromatic enol form ketone group (active methylene group)-containing compounds, preferably the compounds wherein the coupler group A' is represented by the following general formulas (IX), (X), (XI), (XII), (XIII), (XIV), (XV), (XVI) and (XVII):

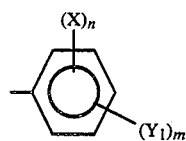
(IX)

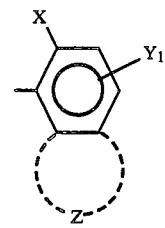
(X)

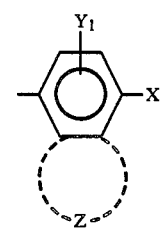
(XI)

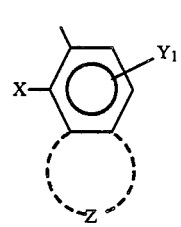
(XII)

[wherein, X, $Y_1$, Z, m and n in the above formulas (IX), (X), (XI) and (XII) each stands for the following:

X: —OH,

or —NHSO$_2$—R$_3$ ($R_1$ and $R_2$ each stands for hydrogen or a substituted or unsubstituted alkyl group, and $R_3$ stands for a substituted or unsubstituted alkyl group or a substituted or unsubstituted aryl group.)

$Y_1$: hydrogen, halogen, a substituted or unsubstituted alkyl group, a substituted or unsubstituted alkoxy group, a carboxy group, a sulfo group, a substituted or unsubstituted sulfamoyl group,

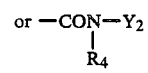

($R_4$ stands for hydrogen, an alkyl group or its substitution product, and a phenyl group or its substitution product, and $Y_2$ stands for a hydrocarbon ring group or its substitution product, a heterocyclic group or its substitution product,

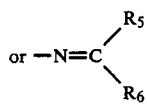

(wherein, $R_5$ stands for a hydrocarbon ring group or its substitution product, a heterocyclic group or its substitution product or a styryl group or its substitution product, $R_6$ stands for hydrogen, an alkyl group, a phenyl group or its substitution product, or $R_5$ and $R_6$ may form a ring in cooperation with carbon atoms bonded thereto.)

Z: a hydrocarbon ring or its substitution product or a heterocyclic ring or its substitution product.]

n: an integer of 1 or 2
m: an integer of 1 or 2

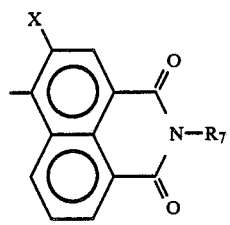 (XIII)

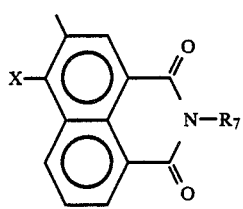 (XIV)

[in the formulas (XIII) and (XIV), $R_7$ stands for a substituted or unsubstituted hydrocarbon group and X is the same as defined above.]

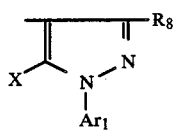 (XV)

[wherein, $R_8$ stands for an alkyl group, a carbamoyl group, a carboxyl group or its ester, $Ar_1$ stands for a hydrocarbon ring group or its substitution product, and X is the same as defined above.]

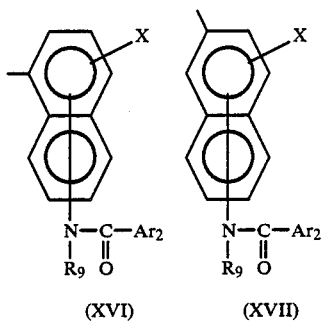

(XVI)   (XVII)

[in the above formulas (XVI) and (XVII), $R_9$ stands for hydrogen or a substituted or unsubstituted hydrocarbon group, and $Ar_2$ stands for a hydrocarbon ring group or its substitution product.]

In said general formula (X), (XI) or (XII), as the hydrocarbon ring there can be enumerated a benzene ring, a naphthalene ring or the like, and as the hetero-ring there can be enumerated an indole ring, a carbazole ring, a benzofuran ring or the like. And, as the substituent on the ring of Z there can be enumerated halogen atoms such as a chlorine atom, a bromine atom and the like.

As the hydrocarbon ring group in $Y_2$ or $R_5$ there can be enumerated a phenyl group, a naphthyl group, an anthryl group, a pyrenyl group and the like, and as the hetero-ring groups there can be enumerated a pyridyl group, a thienyl group, a furyl group, an indolyl group, a benzofuranyl group, a carbazolyl group, a dibenzofuranyl group and the like. Further, as the ring formed by bonding $R_5$ with $R_6$ there can be enumerated a fluorene ring and the like.

As the substituents on the ring formed by the hydrocarbon ring group or hetero-ring group of $Y_2$ or by the cooperation of $R_5$ and $R_6$ there can be enumerated an alkyl group such as a methyl group, an ethyl group, a propyl group, a butyl group or the like, an alkoxy group such as methoxy group, an ethoxy group, a propoxy group, a butoxy group or the like, a halogen atom such as a chlorine atom a bromine atom or the like, a dialkylamino group such as a dimethylamino group, a diethylamino group or the like, a diaralkylamino group such as a dibenzylamino group or the like, a halomethyl group such as a trifluoromethyl group or the like, a nitro group, a cyano group, a carboxyl group or its ester, a hydroxy group, a sulfonic salt group such as $-SO_3Na$ or the like.

As the substituent on the phenyl group represented by $R_4$ there can be enumerated halogen atoms such as a chlorine atom, a bromine atom or the like.

As the typical examples of the hydrocarbon groups represented by $R_7$ or $R_9$ there can be enumerated an alkyl group such as a methyl group, an ethyl group, a propyl group, a butyl group or the like, an aralkyl group such as a benzyl group or the like, an aryl group such as a phenyl group or the like or esters thereof.

As the substituent on the hydrocarbon group represented by $R_7$ or $R_9$ there can be enumerated an alkyl group such as a methyl group, an ethyl group, a propyl group, a butyl group or the like, an alkoxy group such as a methoxy group, an ethoxy group, a propoxy group, a butoxy group or the like, a halogen atom such as a chlorine atom, a bromine atom or the like, a hydroxyl group, a nitro group or the like.

As the hydrocarbon ring group in $Ar_1$ or $Ar_2$ there can be typically enumerated a phenyl group or a naphthyl group. And, the constituents on these groups include an alkyl group such as a methyl group, an ethyl group, a propyl group, a butyl group or the like, an alkoxy group such as a methoxy group, an ethoxy group, a propoxy group, a butoxy or the like, a nitro group, a halogen atom such as chlorine atom, a bromine atom or the like, a cyano group, a dialkylamino group such as dimethylamino group, a diethylamino group and the like.

Of the couplers represented by X, the hydroxyl group is the most suitable one.

Of the above enumerated coupler groups, the most preferable ones are those belonging to the above mentioned general formulas (X), (XIII), (XIV), (XV), (XVI) and (XVII). Among them, the hydroxyl group belonging to the general formula (X) is preferable. Among them, the coupler group represented by the general formula (XVIII) is preferable:

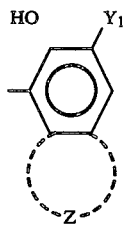

(wherein, $Y_1$ and Z are the same as defined above.)

More preferable is the one represented by the general formula (XIX):

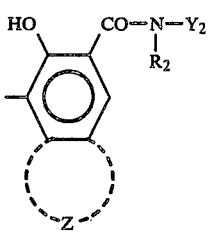

(wherein, Z, $Y_2$ and $R_2$ are the same as defined above.)

Still further, among the above mentioned preferable coupler groups, those represented by the general formulas (XX) or (XXI) are suitable:

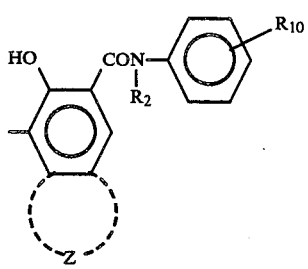 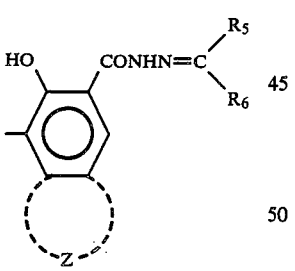

(XX)                    (XXI)

(wherein, Z, $R_2$, $R_5$ and $R_6$ are the same as defined above, and as $R_{10}$ there may be enumerated for instance the above mentioned substituent belonging to $Y_2$.)

The concrete examples of the aforesaid disazo pigments used in the present invention can be shown using structural formulas as follows. For the purpose of simplicity, said structural formulas have been limited only to recite the structural formulas of the coupler groups A' respectively.

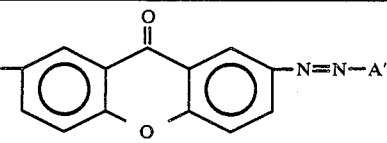

| Disazo Pigment No. | A' |
|---|---|
| 1 | 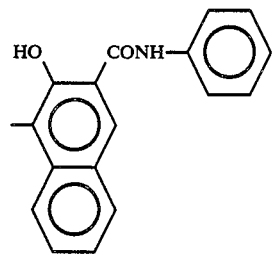 |
| 2 |  |
| 3 | 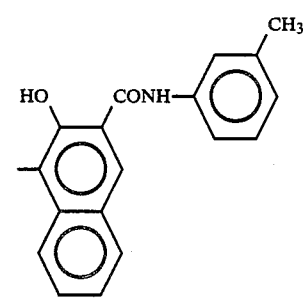 |
| 4 | 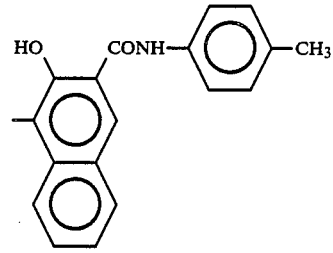 |
| 5 | 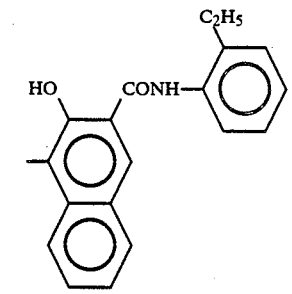 |

-continued
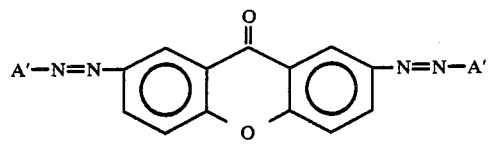
| Disazo Pigment No. | A' |
|---|---|
| 6 | 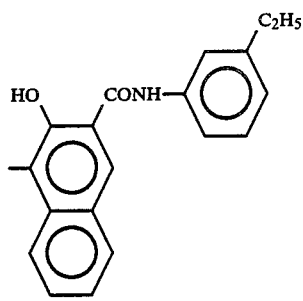 |
| 7 | 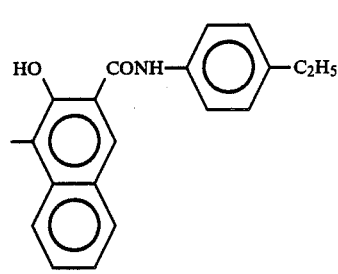 |
| 8 | 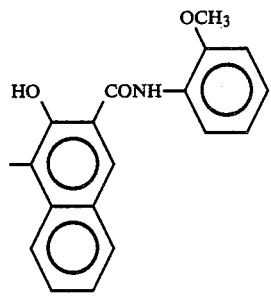 |
| 9 | 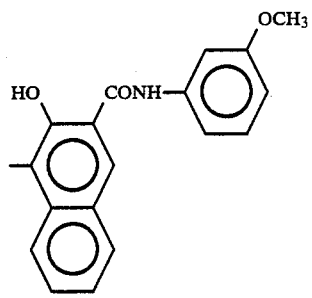 |
-continued
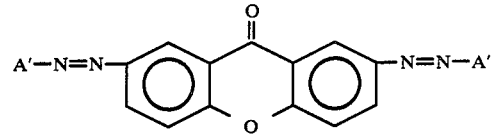
| Disazo Pigment No. | A' |
|---|---|
| 10 | 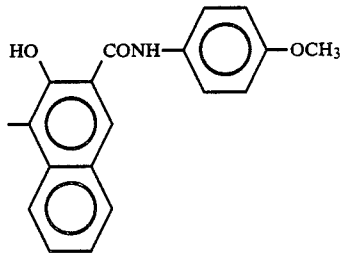 |
| 11 | 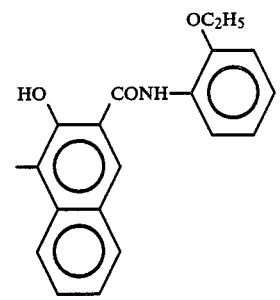 |
| 12 | 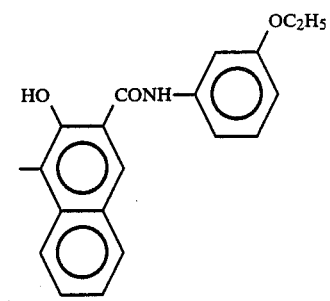 |
| 13 | 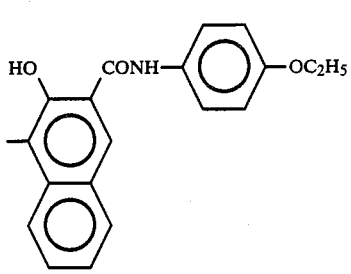 |
| 14 | 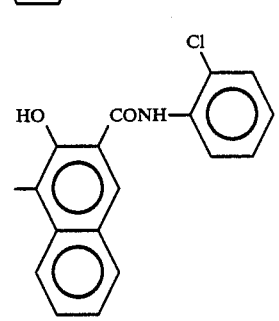 |

-continued
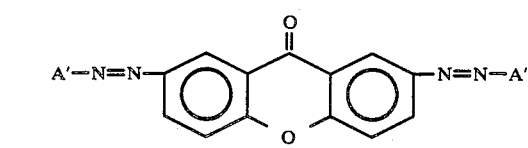
| Disazo Pigment No. | A' |
|---|---|
| 15 | 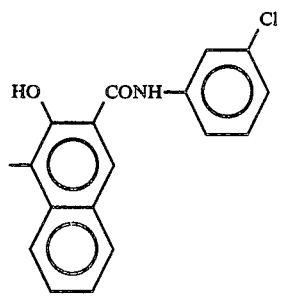 |
| 16 | 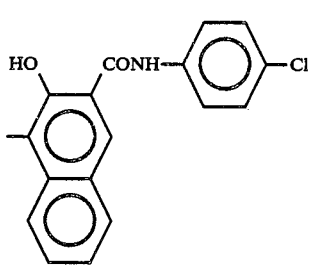 |
| 17 | 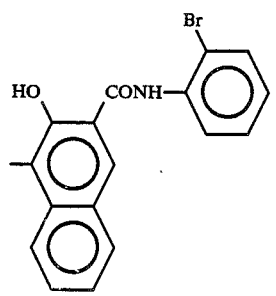 |
| 18 | 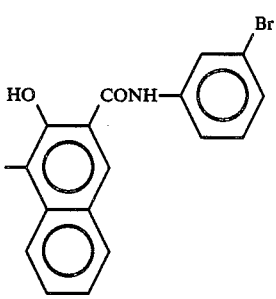 |
-continued
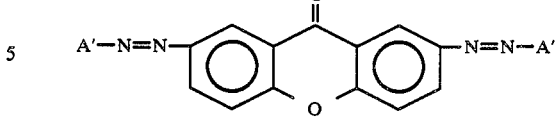
| Disazo Pigment No. | A' |
|---|---|
| 19 | 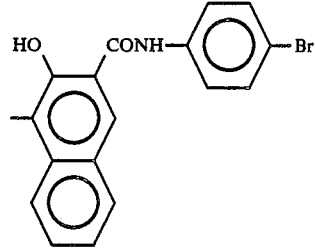 |
| 20 | 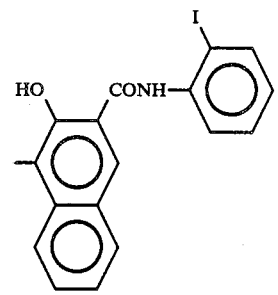 |
| 21 | 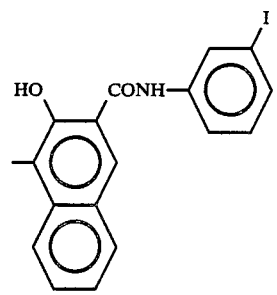 |
| 22 | 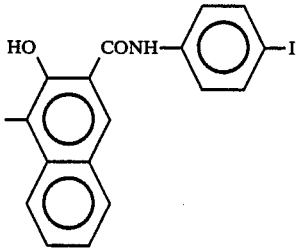 |
| 23 | 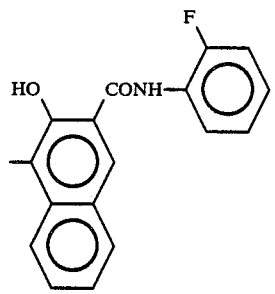 |

-continued
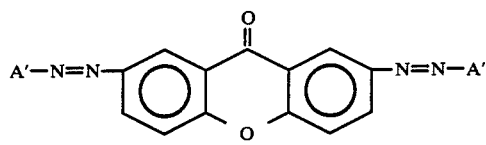
| Disazo Pigment No. | A' |
|---|---|
| 24 | 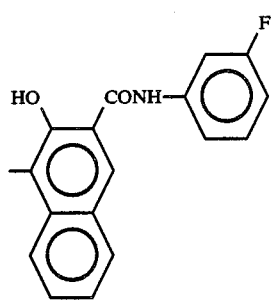 |
| 25 | 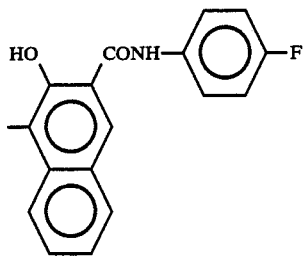 |
| 26 | 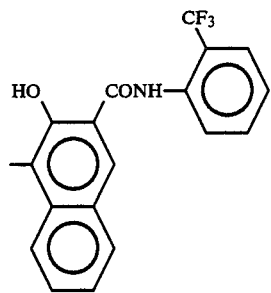 |
| 27 | 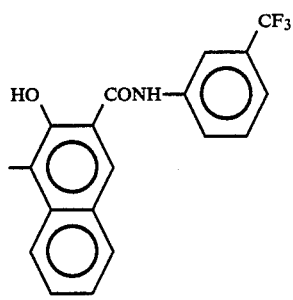 |
-continued
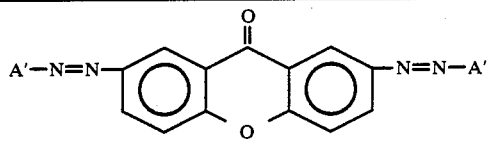
| Disazo Pigment No. | A' |
|---|---|
| 28 | 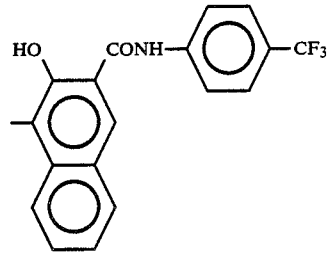 |
| 29 | 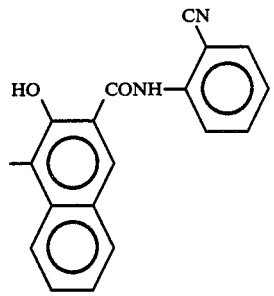 |
| 30 | 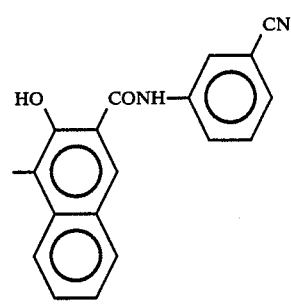 |
| 31 | 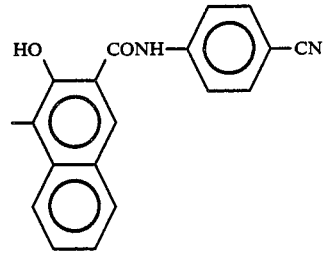 |
| 32 | 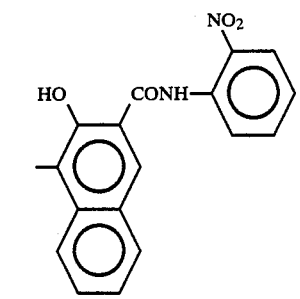 |

-continued
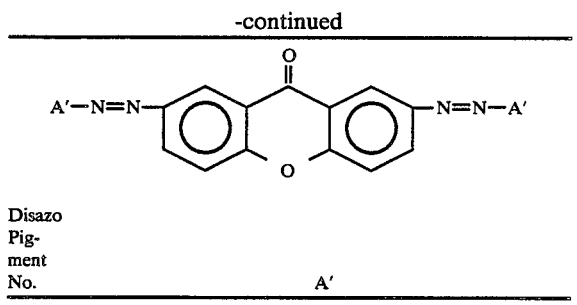
| Disazo Pigment No. | A' |
|---|---|
| 33 | 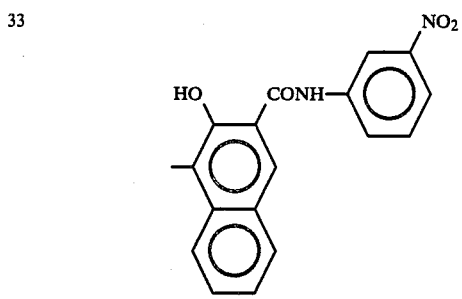 |
| 34 | 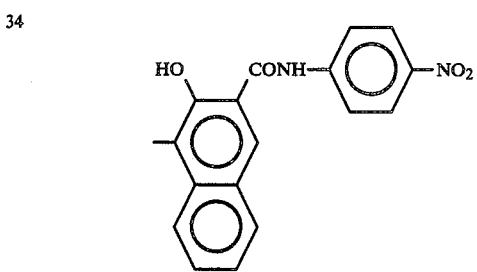 |
| 35 | 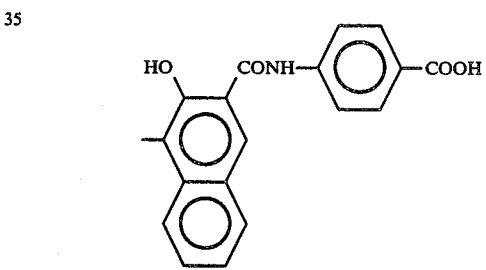 |
| 36 | 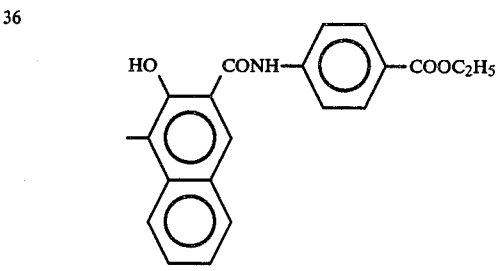 |
| 37 | 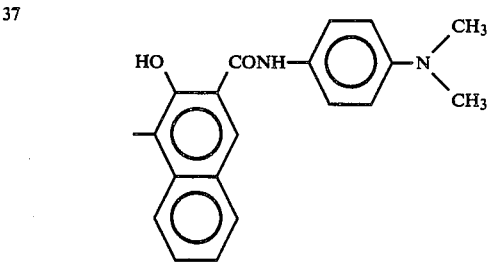 |
-continued
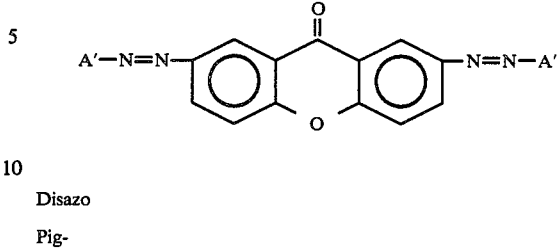
| Disazo Pigment No. | A' |
|---|---|
| 38 | 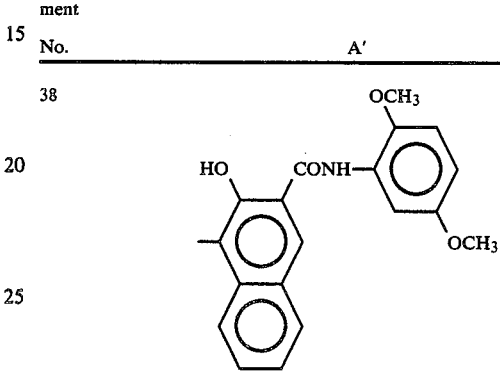 |
| 39 | 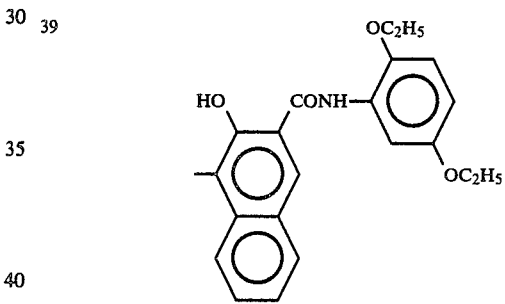 |
| 40 | |
| 41 | |

-continued
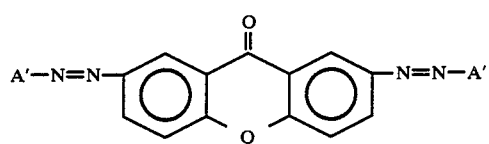
| Disazo Pigment No. | A' |
|---|---|
| 42 | 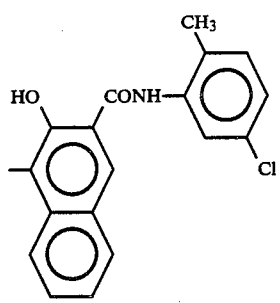 |
| 43 | 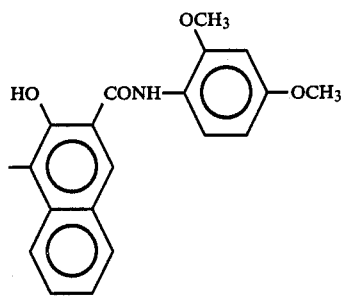 |
| 44 | 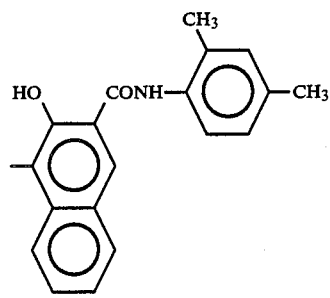 |
| 45 | 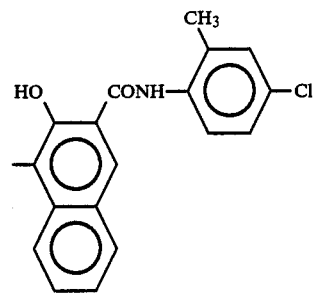 |
-continued
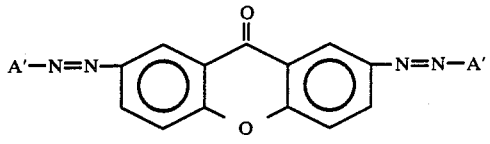
| Disazo Pigment No. | A' |
|---|---|
| 46 | 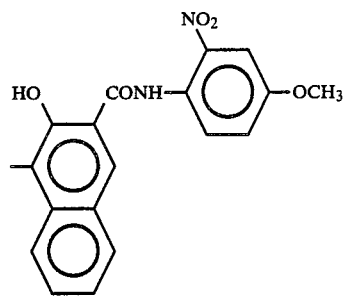 |
| 47 | 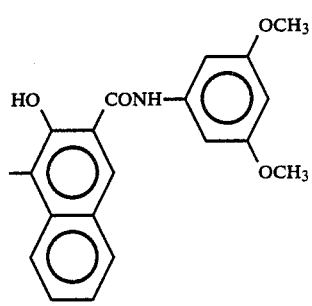 |
| 48 | 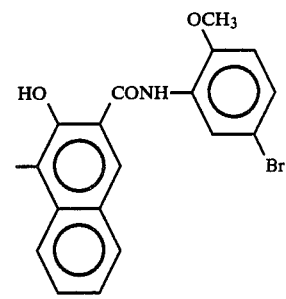 |
| 49 | 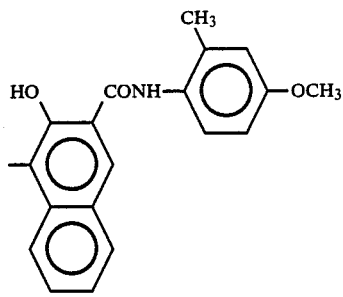 |

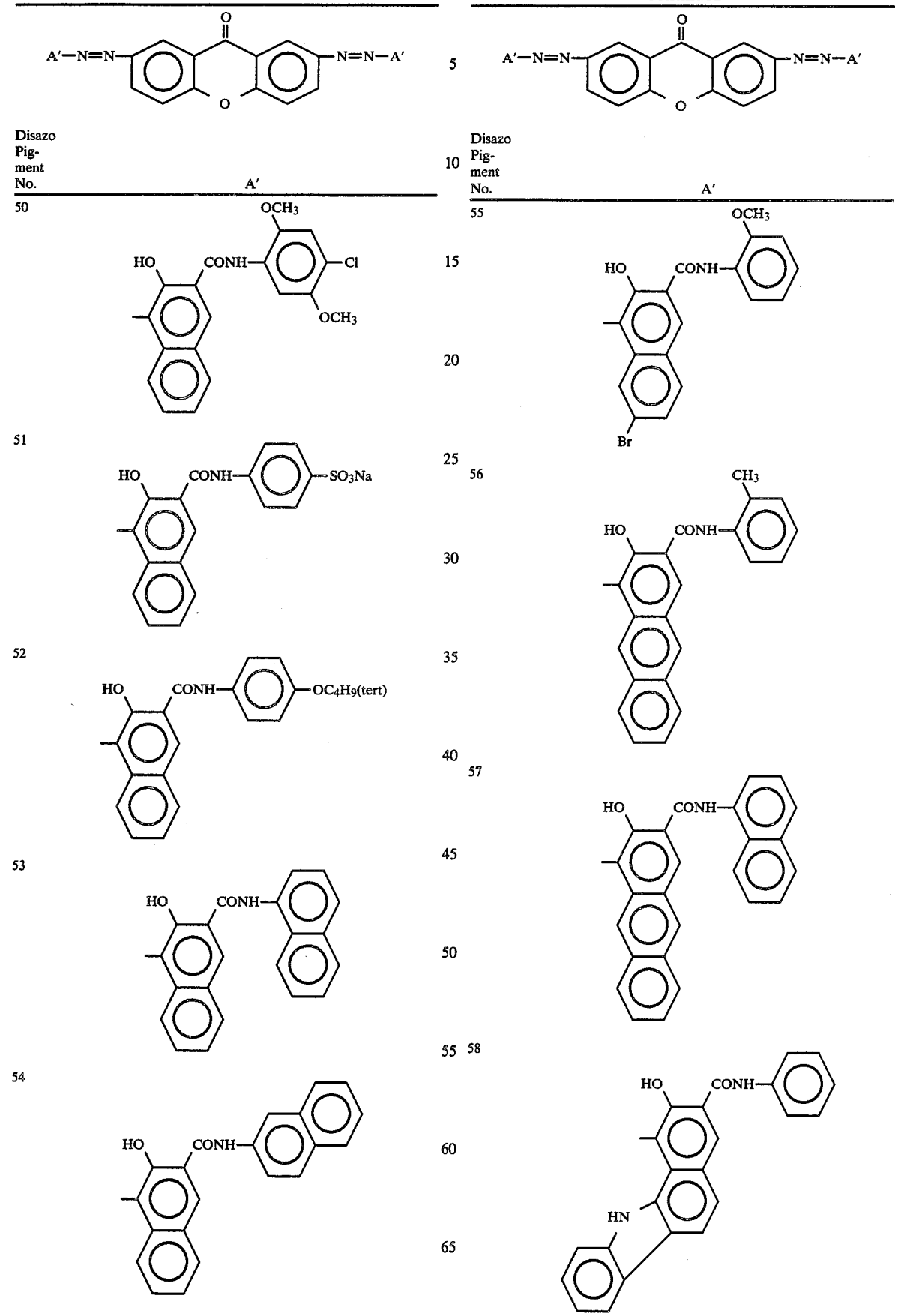

-continued
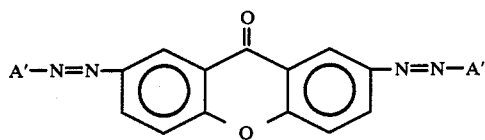
| Disazo Pigment No. | A' |
|---|---|
| 59 | 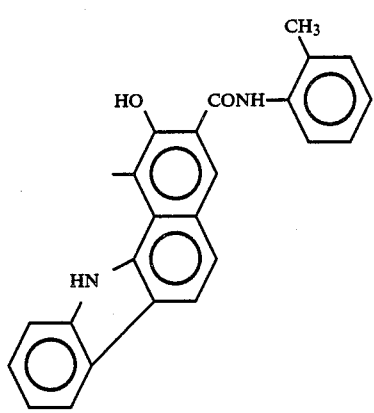 |
| 60 | 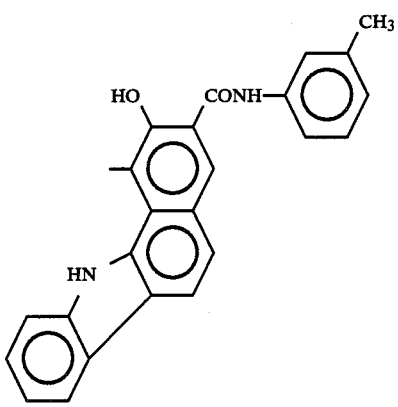 |
| 61 | 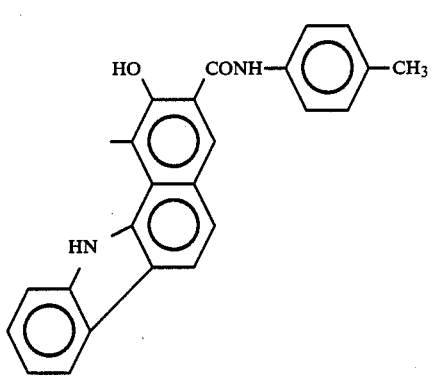 |
-continued
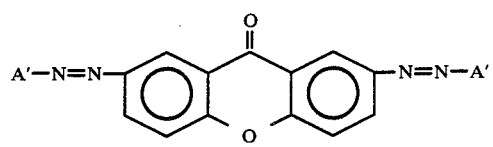
| Disazo Pigment No. | A' |
|---|---|
| 62 | 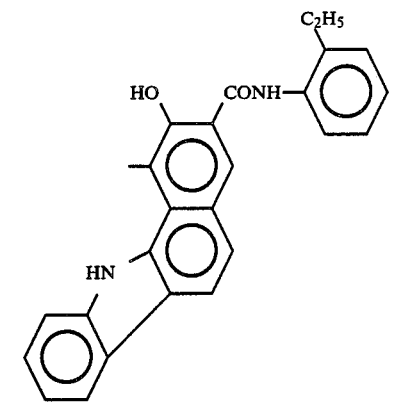 |
| 63 | 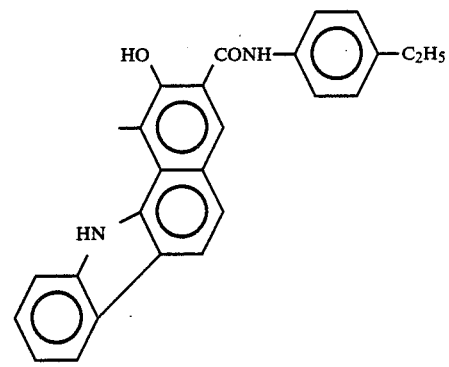 |
| 64 | 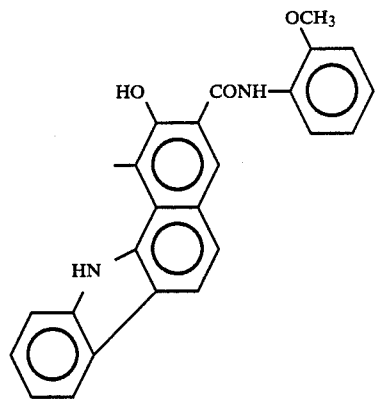 |

-continued
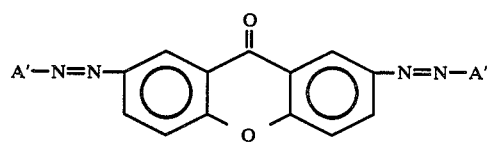
Disazo Pigment No. | A'
---|---
65 | 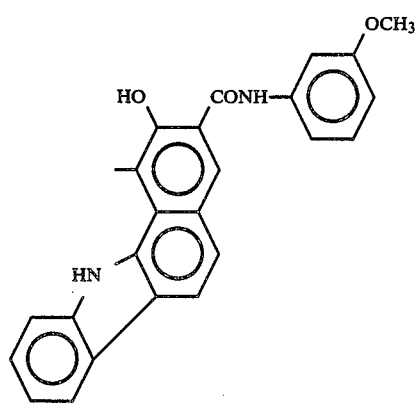
66 | 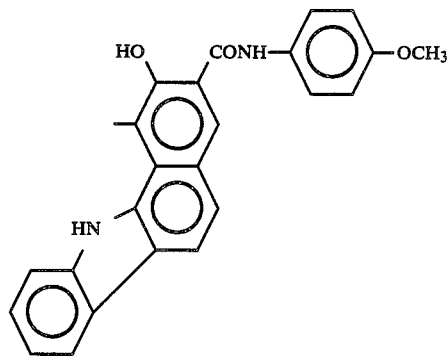
67 | 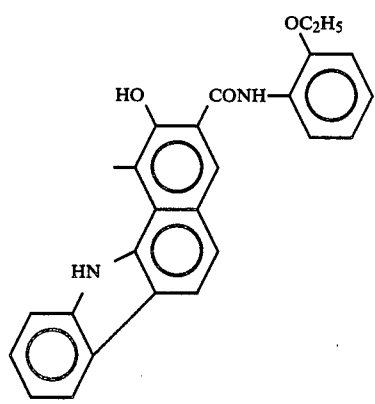
-continued
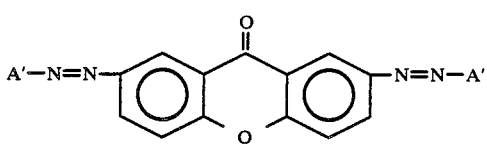
Disazo Pigment No. | A'
---|---
68 | 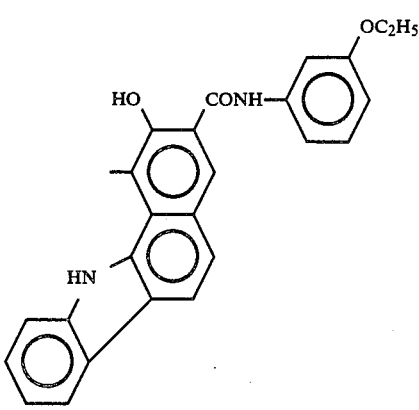
69 | 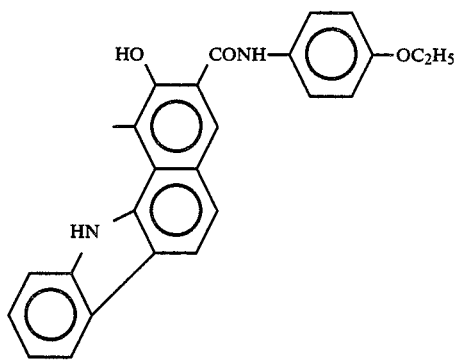
70 | 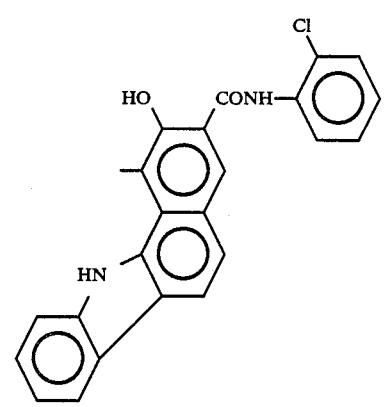

-continued
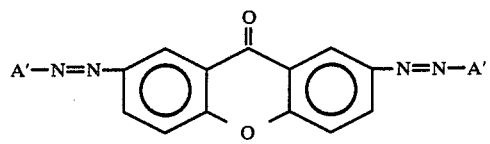
| Disazo Pigment No. | A' |
|---|---|
| 71 | 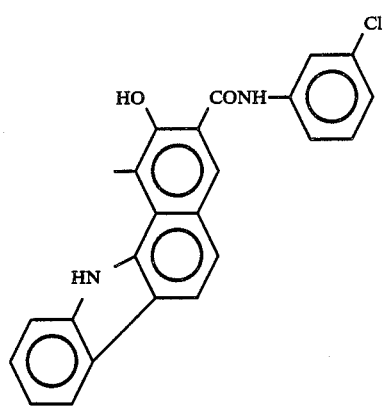 |
| 72 | 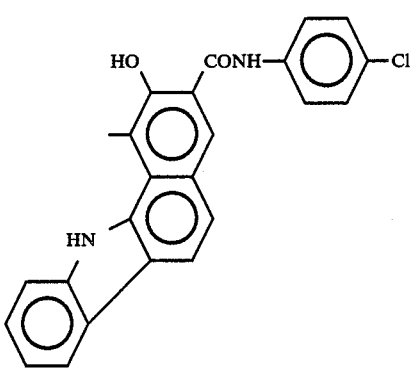 |
| 73 | 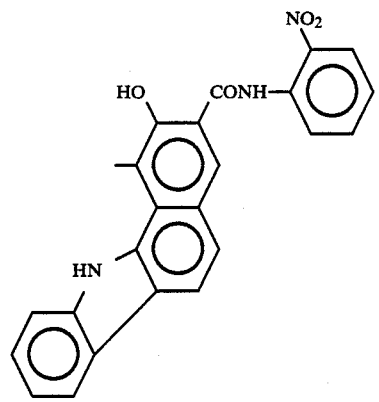 |
-continued
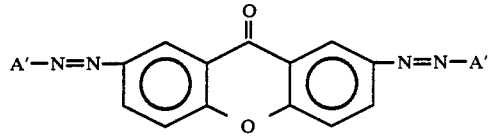
| Disazo Pigment No. | A' |
|---|---|
| 74 | 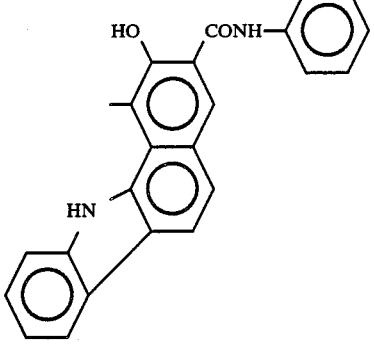 |
| 75 | 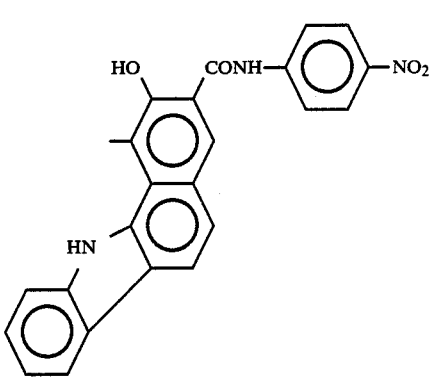 |
| 76 | 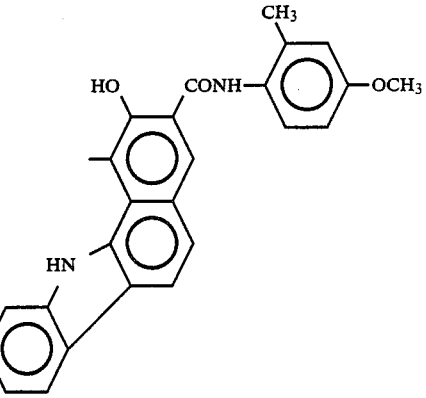 |
| 77 |  |

-continued
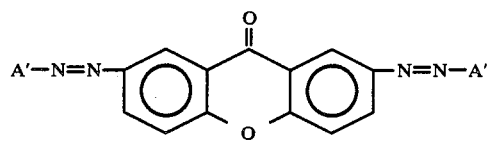
| Disazo Pigment No. | A' |
|---|---|
| 78 | 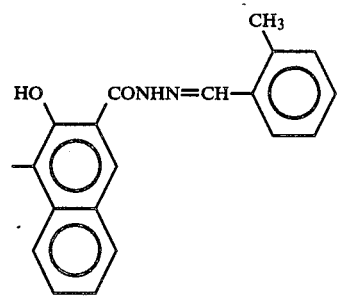 |
| 79 | 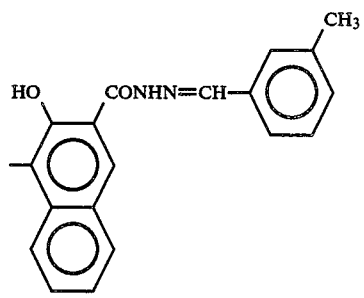 |
| 80 | 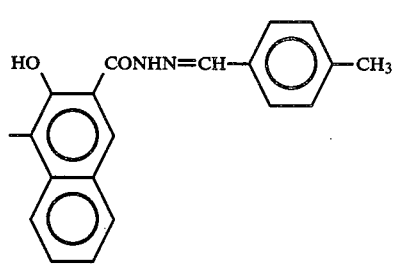 |
| 81 | 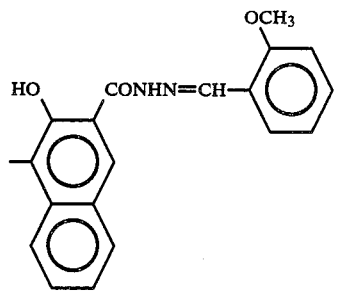 |
-continued
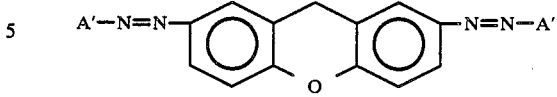
| Disazo Pigment No. | A' |
|---|---|
| 82 | 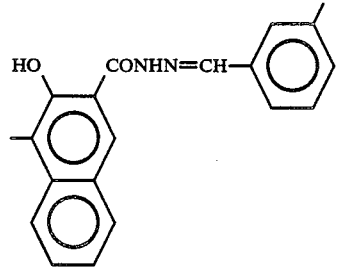 |
| 83 | 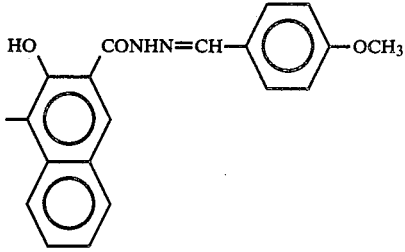 |
| 84 | 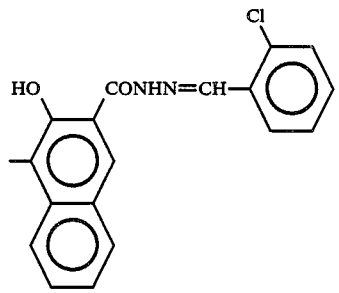 |
| 85 | 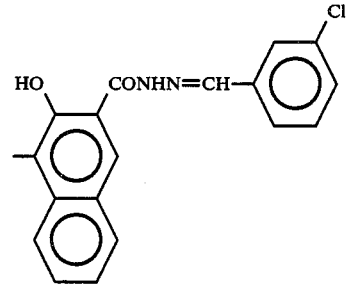 |
| 86 | 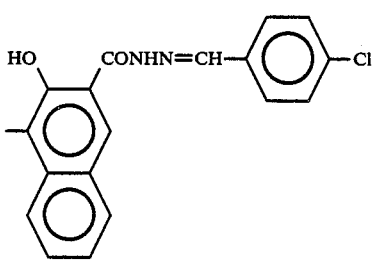 |

-continued
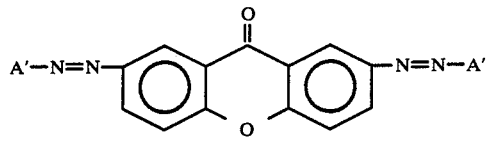
| Disazo Pigment No. | A' |
|---|---|
| 87 | 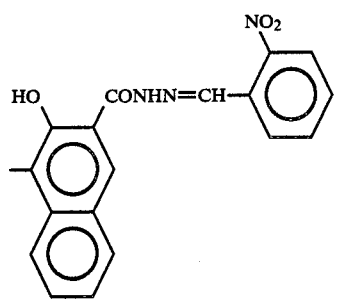 |
| 88 | 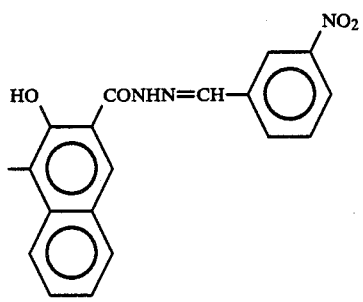 |
| 89 | 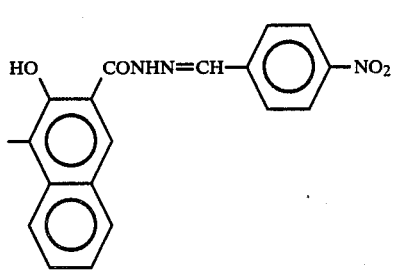 |
| 90 | 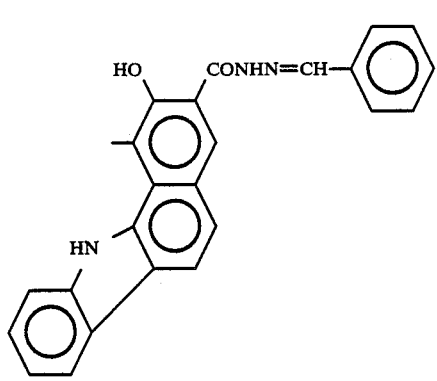 |
-continued
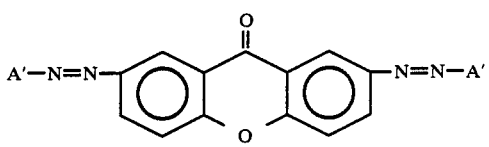
| Disazo Pigment No. | A' |
|---|---|
| 91 | 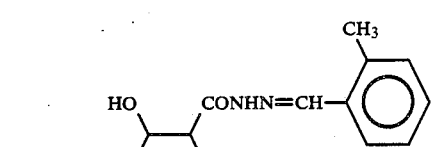 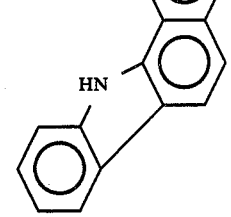 |
| 92 | 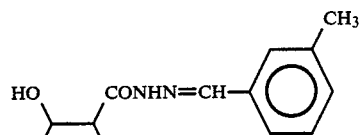 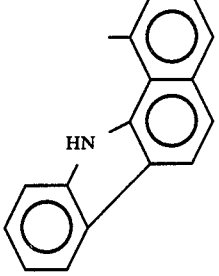 |
| 93 | 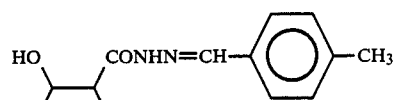 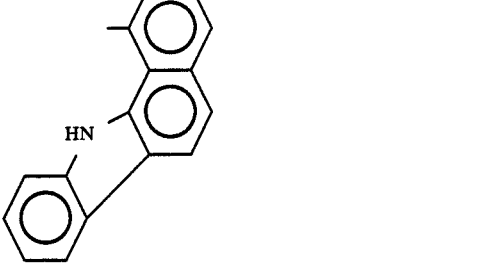 |

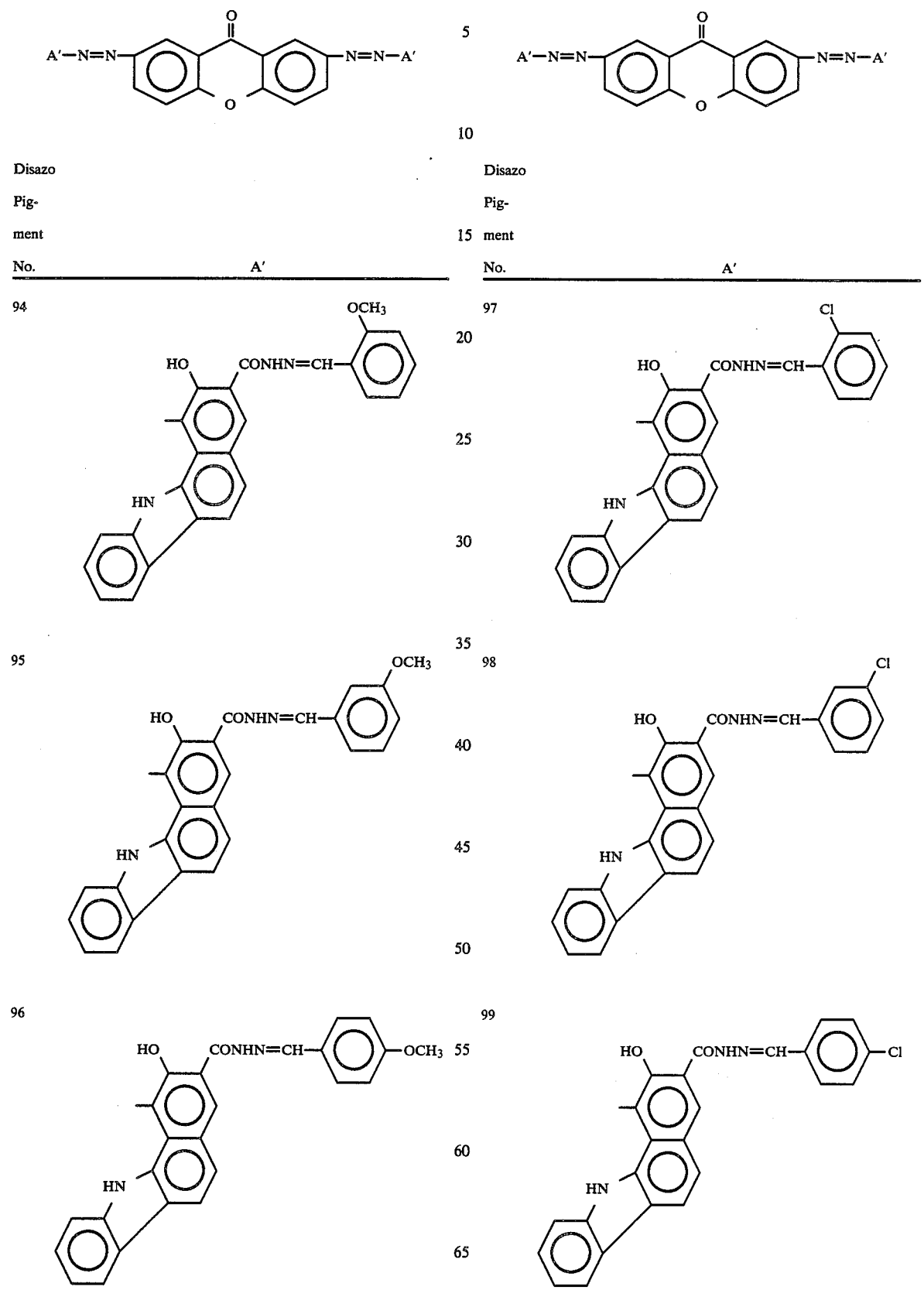

-continued
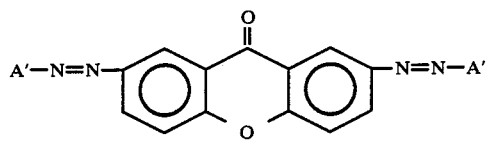
| Disazo Pigment No. | A' |
|---|---|
| 100 | 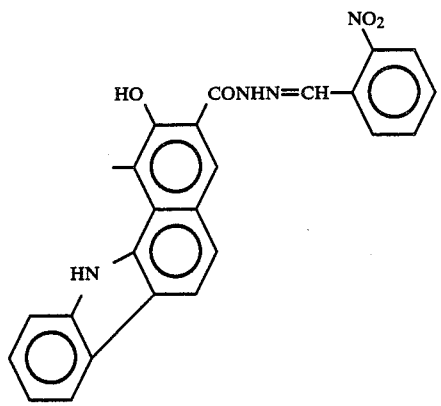 |
| 101 | 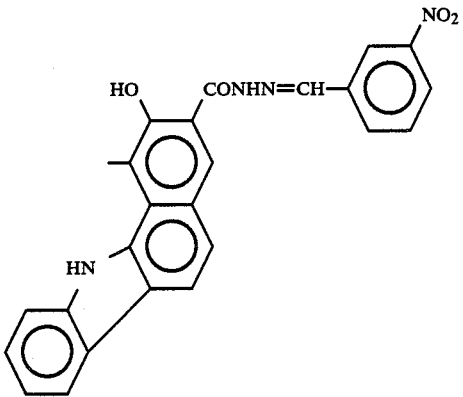 |
| 102 | 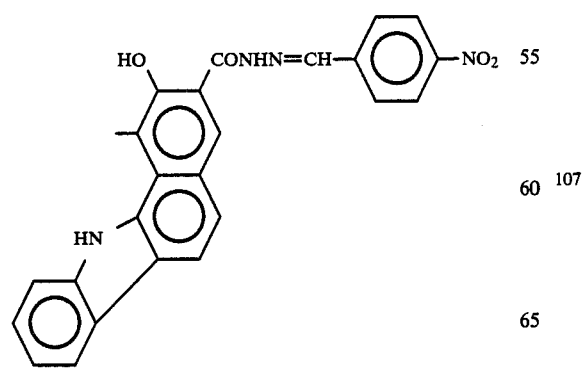 |
-continued
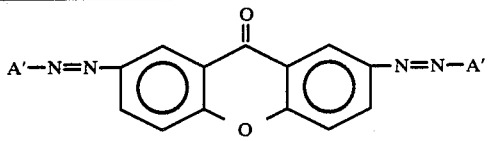
| Disazo Pigment No. | A' |
|---|---|
| 103 | 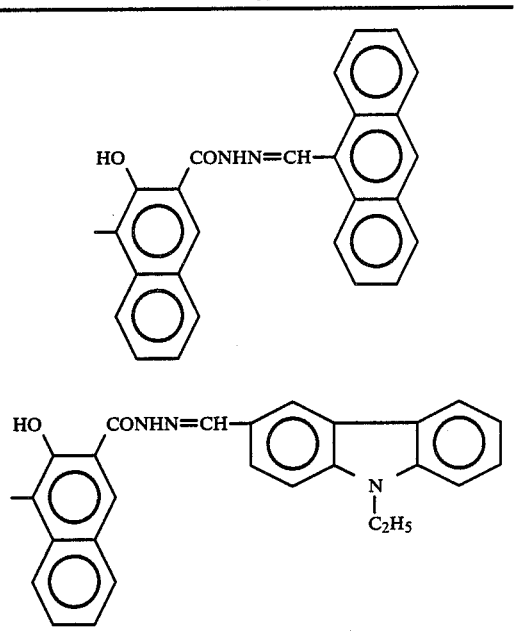 |
| 104 | |
| 105 | |
| 106 | 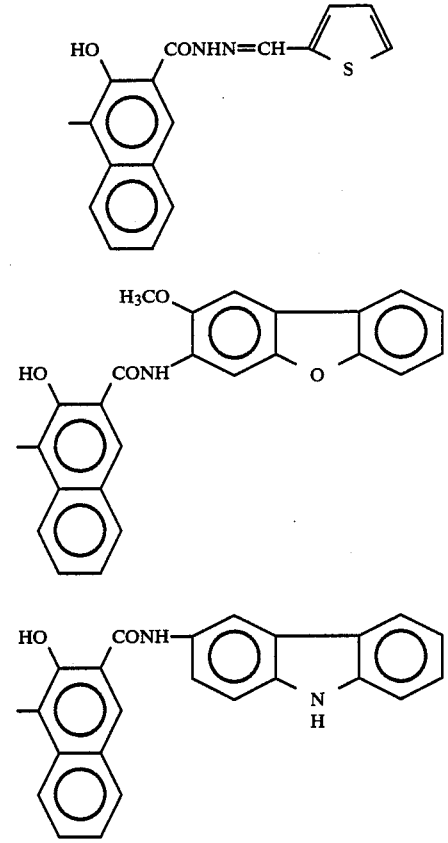 |
| 107 | |

-continued
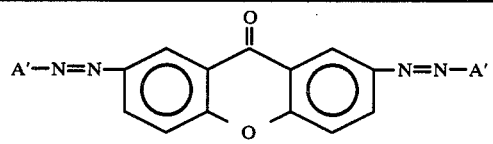
| Disazo Pigment No. | A' |
|---|---|
| 108 | 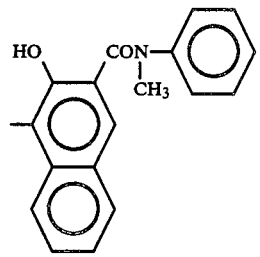 |
| 109 | 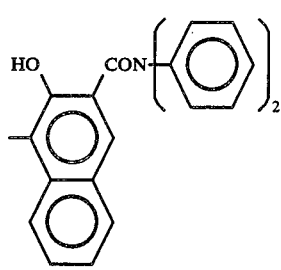 |
| 110 | 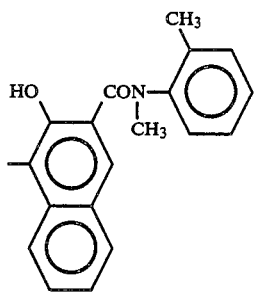 |
| 111 | 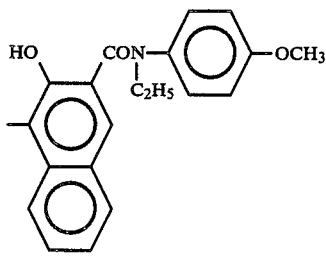 |
| 112 | 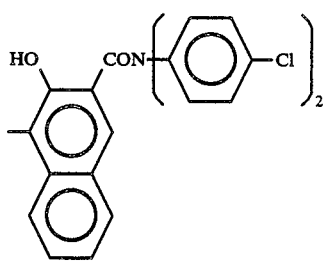 |
-continued
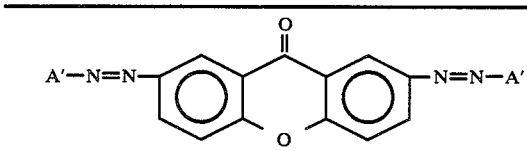
| Disazo Pigment No. | A' |
|---|---|
| 113 | 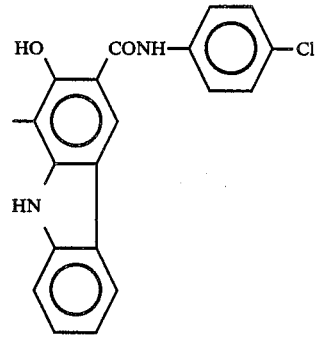 |
| 114 | 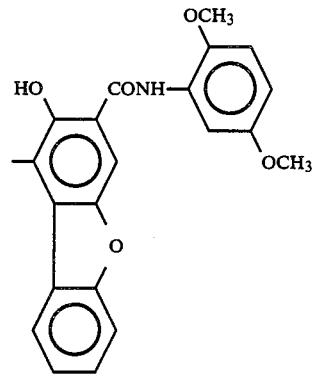 |
| 115 | 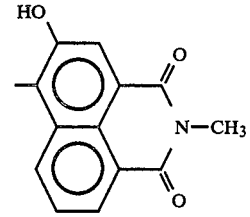 |
| 116 | 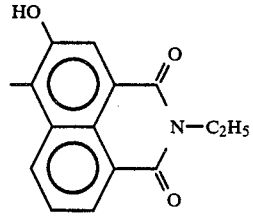 |
| 117 | 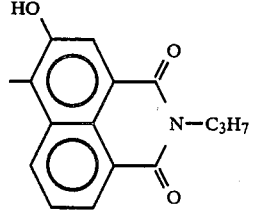 |

-continued
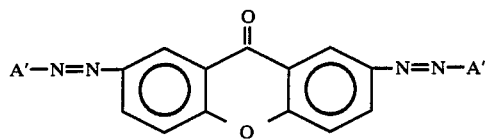
| Disazo Pigment No. | A' |
|---|---|
| 118 | 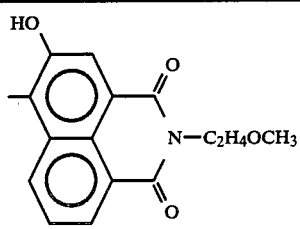 |
| 119 | 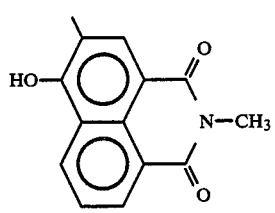 |
| 120 | 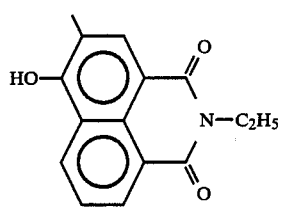 |
| 121 | 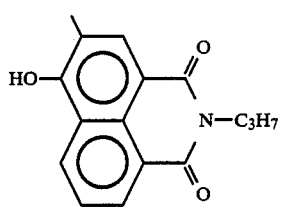 |
| 122 | 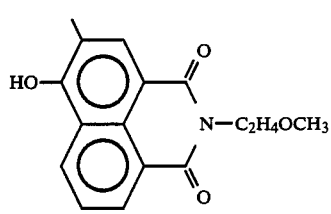 |
| 123 | 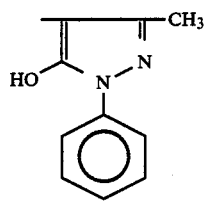 |
-continued
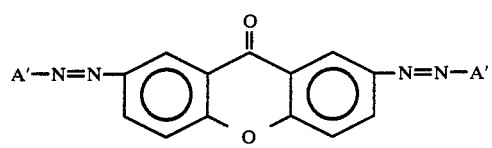
| Disazo Pigment No. | A' |
|---|---|
| 124 | 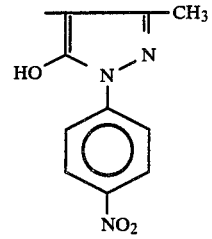 |
| 125 | 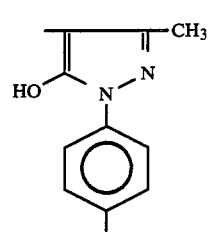 |
| 126 | 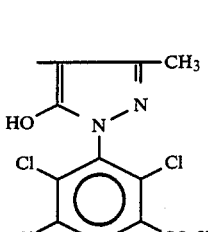 |
| 127 | 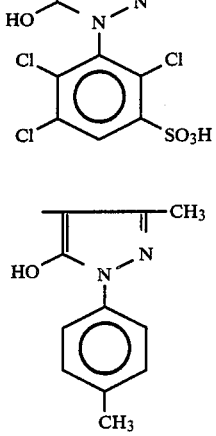 |
| 128 | 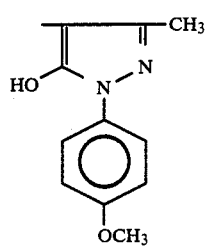 |

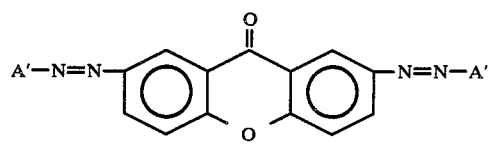
-continued
| Disazo Pigment No. | A' |
|---|---|
| 129 | 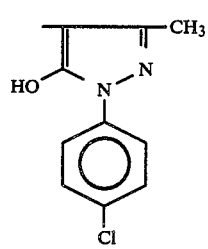 |
| 130 | 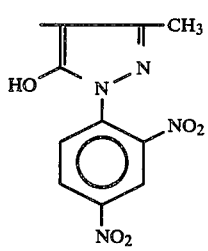 |
| 131 | 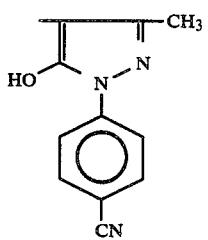 |
| 132 | 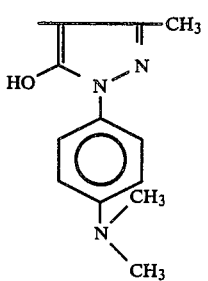 |
| 133 | 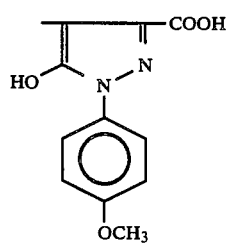 |
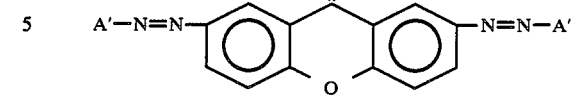
-continued
| Disazo Pigment No. | A' |
|---|---|
| 134 | 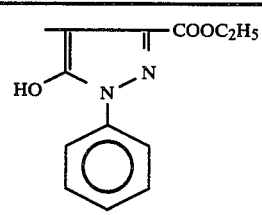 |
| 135 | 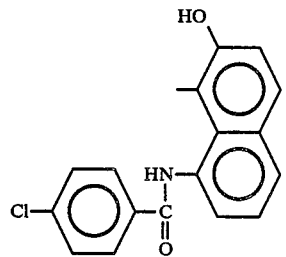 |
| 136 | 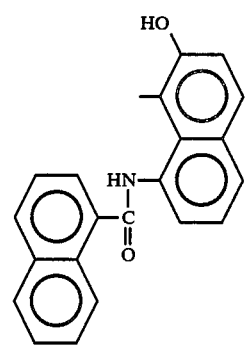 |
| 137 | 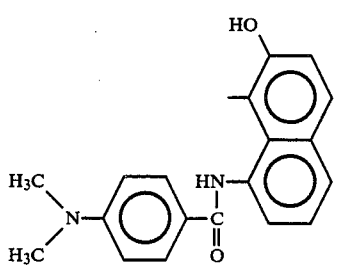 |
| 138 | 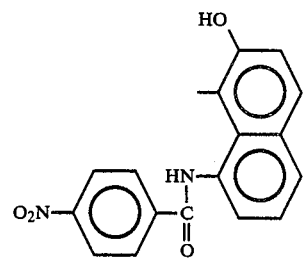 |

-continued
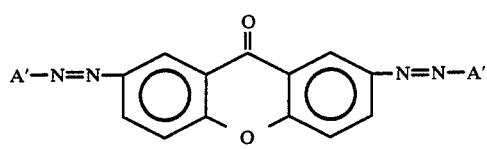
| Disazo Pigment No. | A' |
|---|---|
| 139 | 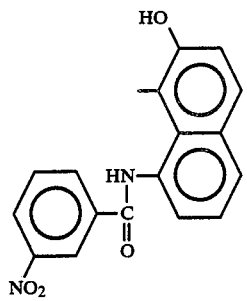 |
| 140 | 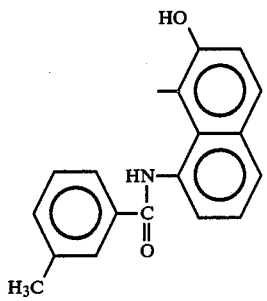 |
| 141 | 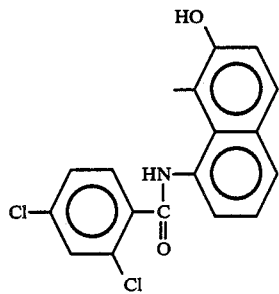 |
| 142 | 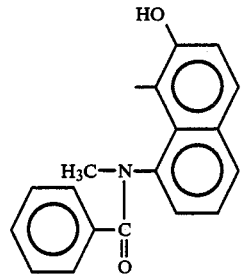 |
-continued
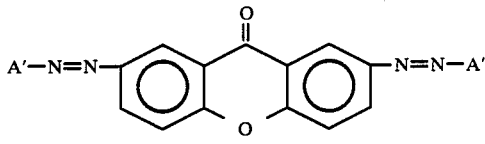
| Disazo Pigment No. | A' |
|---|---|
| 143 | 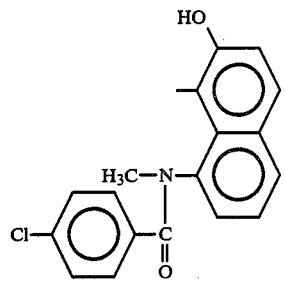 |
| 144 | 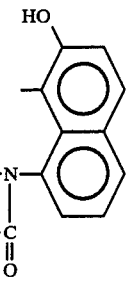 |
| 145 | 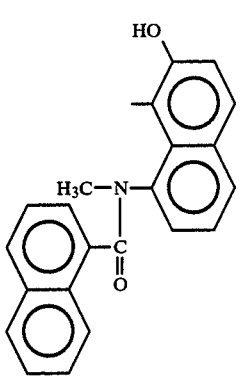 |
| 146 | 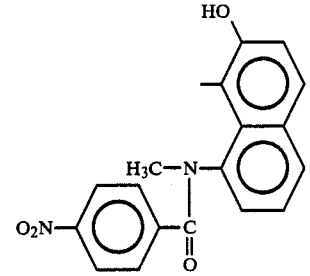 |

| | |
|---|---|
| 63 | 64 |
| -continued | -continued |
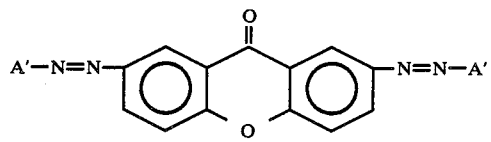
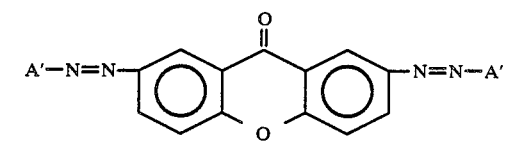
| Disazo Pigment No. | A' |
|---|---|
| 147 | 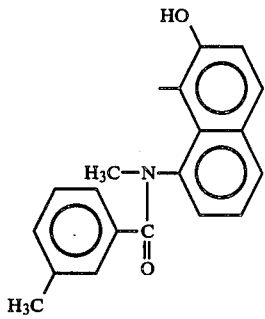 |
| 148 | 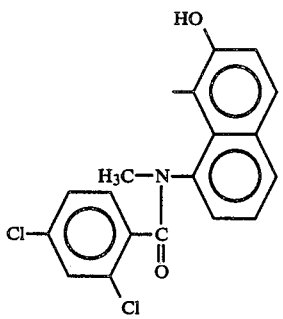 |
| 149 | 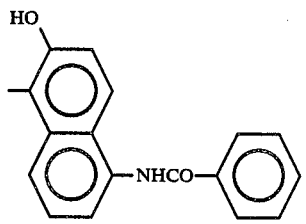 |
| 150 | 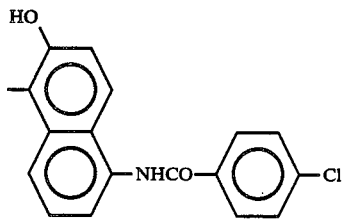 |
| 151 | 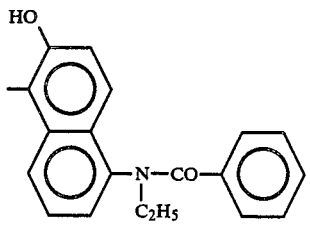 |
| Disazo Pigment No. | A' |
|---|---|
| 152 | 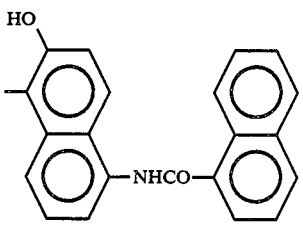 |
| 153 | 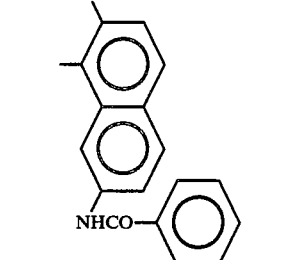 |
| 154 | 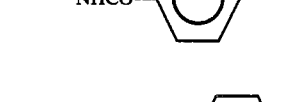 |
| 155 | 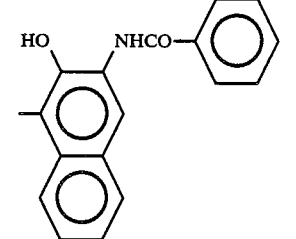 |
| 156 | 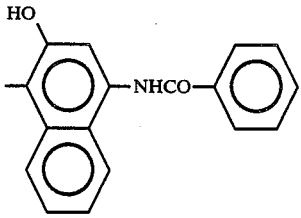 |

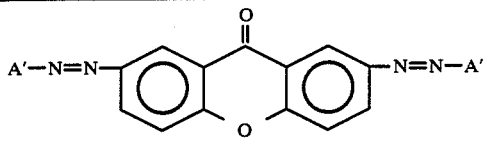

| Disazo Pigment No. | A' |
|---|---|
| 157 | 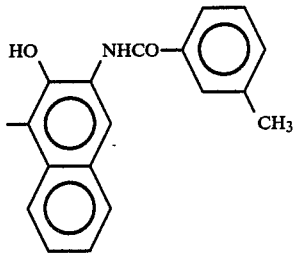 |
| 158 | 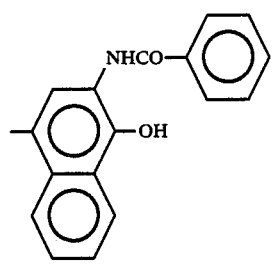 |
| 159 | 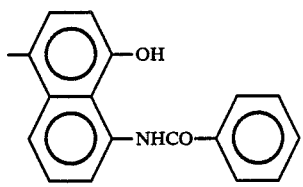 |
| 160 | 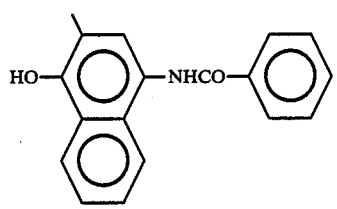 |
| 161 | 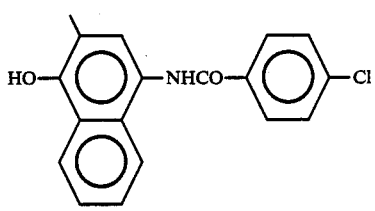 |
| 162 | 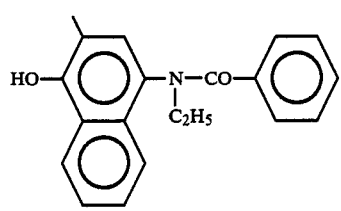 |

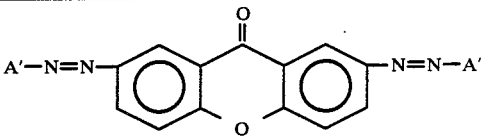

| Disazo Pigment No. | A' |
|---|---|
| 163 | 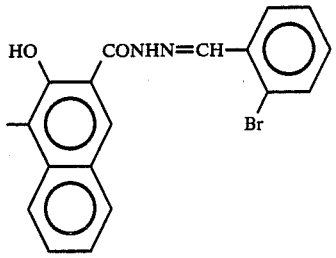 |
| 164 | 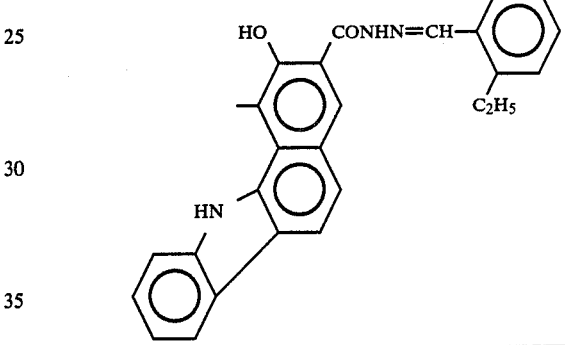 |

The use of above mentioned disazo compounds according to the present invention can readily produce extremely high-sensitive electrophotographic elements. Among them, Disazo compound Nos. 14, 17, 20, 23, 26, 29, 58, 84 and 90 are especially preferable.

These disazo compounds can be prepared according to the exactly same procedure as described above. That is, said disazo compounds can be readily prepared by diazotating 2,7-diaminoxanthone in a normal manner to thereby obtain tetrazonium salt, and then subjecting this salt and couplers corresponding thereto, to a coupling reaction in a proper solvent such, for instance, as N,N-dimethyl-formamide under the influence of a base.

In the electrophotographic element according to the present invention, the disazo compound is used as the charge carrier generating material in the photosensitive layer. The typical construction of this electrophotographic element was shown in FIG. 3 and FIG. 4.

The electrophotographic element shown in FIG. 3 is the one comprising an electrically conductive substrate 11 and a multi-layer type photosensitive layer 19, formed on said substrate, which comprises a charge carrier generating layer 15 consisting essentially of a disazo compound 13 and a charge transfer layer 17 consisting essentially of a charge transfer compound and an insulating binder.

In the electrophotographic element shown in FIG. 3, the imagewise irradiation transmits through the charge transfer layer and reaches the charge carrier generating layer 15 where charge carriers are generated by the aid of disazo compound 13 contained therein, while the charge transfer layer 17 is injected with charge carriers and transfers them. That is, the said electrophotographic element has such a mechanism that the disazo compound 13 takes part in generating charge carriers required for light decay and the charge transfer 17 takes part in transferring said charge carriers.

The electrophotographic element shown in FIG. 4 comprises an electrically conductive substrate 11 and a monolayer type photosensitive layer 19, formed on said substrate, which is consisted essentially of a disazo compound 13, a charge transfer material and an insulating binder, wherein said disazo compound 13 is a charge carrier generating material. As another electrophotographic element, there can be enumerated the one obtained by reversing the order of the charge carrier generating layer and the charge transfer layer in the electrophotographic element of FIG. 3.

In the photosensitive layer of FIG. 3, the charge carrier generating layer 15 is preferably 0.01 to 5μ thick, more preferably 0.05 to 2μ. In case this thickness is less than 0.01, charge carriers are not generated to the full, while in case this thickness is more than 5μ, the residual electric potential is too high to be used practically. The thickness of the charge transfer layer 17 is preferably 3 to 50μ, more preferably 5 to 20 μ. In case this thickness is less than 3μ, the chargeability is insufficient, while the same thickness is more than 50μ, the residual electric potential is too high to be used practically. The charge carrier generating layer 15 is consisted essentially of the disazo compound represented by the above mentioned general formula and further can contain a binder, a plasticizer and the like. The percentage of the disazo compound in the charge carrier generating is preferably 30 to 100 wt.%, more preferably 50 wt.% or more. The charge transfer layer 17 is consisted essentially of a charge transfer material and a binder, and may further contain a plasticizer and the like. The percentage of the charge transfer material in the charge transfer layer is 10 to 95 wt.%, preferably 30 to 90 wt.%. In case the percentage occupied by the charge transfer material is less than 10 wt.%, the charge transfer operation is hardly conducted, while said percentage is more than 95 wt.%, the mechanical strength of the element film is extremely inferior and so can not be put to practical use.

In the case of the element shown in FIG. 4, the thickness of the photosensitive layer 19' is preferably 3 to 50μ, more preferably 5 to 20μ. The percentage of the disazo compound in the photosensitive layer 19' is preferably 50 to 0.1 wt.%, more preferably 20 wt.% or less, and the percentage of the charge transfer material is preferably 10 to 95 wt.%, more preferably 30 to 90 wt.%.

Next, other constitutional materials used in the electrophotographic element according to the present invention may be explained concretely.

Firstly, as the electrically conductive substrate used therein there can be enumerated metal plates of aluminum, copper, zinc and the like, those obtained by vapor-depositing electrically conductive materials such as aluminum, $SnO_2$ and the like on plastic sheets or plastic films of polyester and the like, or electrically conductive-treated paper and the like.

As the binders used in the present invention there can be enumerated condensation resins such as polyamide, polyurethane, polyester, epoxy resin, polyketone, polycarbonate and the like, vinyl polymers such as polyvinyl ketone, polystyrene, poly-N-vinyl carbazole, polyacrylamide and the like, and so on. In this connection, it is to be noted that the present invention can employ every insulating and adhesive resin.

As the plasticizers there may be enumerated halogenated paraffin, polybiphenyl chloride, dimethylnaphthalene, dibutyl phthalate and the like. There may be added silicone oils for the purpose of bettering the surface-smoothness of the electrophotographic element.

The charge transfer materials used in the present invention include a hole transfer material and an electron transfer material. As the hole transfer material there can be enumerated the compounds represented, for instance, by the following general formulas (1)–(11):

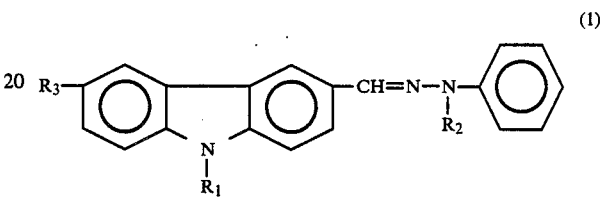
(1)

(wherein, $R_1$ stands for a methyl group, an ethyl group, a 2-hydroxyethyl group or a 2-chloroethyl group, $R_2$ stands for a methyl group, an ethyl group, a benzyl group or a phenyl group, $R_3$ stands for hydrogen, chlorine, bromine, an alkyl group having 1 to 4 carbon atoms, an alkoxy group having 1 to 4 carbon atoms, a dialkylamino group or a nitro group.)

(2)

(wherein, Ar stands for a naphthalene ring, an anthracene ring, a styryl group and their substituents or a pyridine ring, a furan ring and a thiophene ring, and R stands for an alkyl group or a benzyl group.)

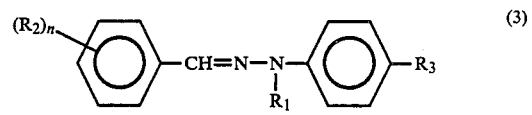
(3)

(wherein, $R_1$ stands for an alkyl group, a benzyl group and a phenyl group, $R_2$ stands for hydrogen, an alkyl group having 1 to 3 carbon atoms, an alkoxy group having 1 to 3 carbon atoms, a dialkylamino group, a diaralkylamino group or a diarylamino group, n stands for an integer of 1 to 4, and in case n is more than 2 $R_2$ may be the same or different. $R_3$ stands for hydrogen or a methoxy group.)

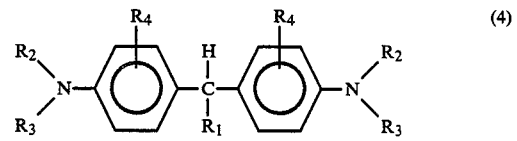
(4)

(wherein, $R_1$ stands for an alkyl group having 1–11 carbon atoms, a substituted or unsubstituted phenyl group or heterocyclic group, $R_2$, $R_3$ may be each the same or different and stands for hydrogen, an alkyl group having 1 to 4 carbon atoms, a hydroxyalkyl group, a chloroalkyl group and a substituted or unsubstituted aralkyl group, and $R_2$ and $R_3$ may be under bond with each other to form a nitrogen-containing heterocyclic ring. And, $R_4$ may be the same or different and stands for hydrogen, an alkyl group having 1 to 4 carbon atoms, an alkoxy group or halogen.)

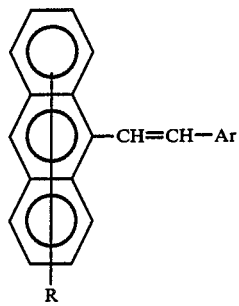
(5)

(wherein, R stands for hydrogen or a halogen atom, and Ar stands for a substituted or unsubstituted phenyl group, naphthyl group, anthryl group or a carbazolyl group.)

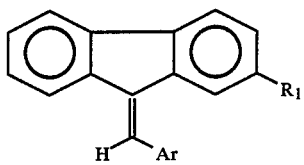
(6)

(wherein, $R_1$ stands for hydrogen, halogen, a cyano group, an alkoxy group having 1 to 4 carbon atoms or an alkyl group having 1 to 4 carbon atoms, Ar stands for

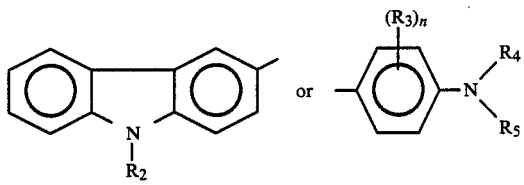

$R_2$ stands for an alkyl group having 1 to 4 carbon atoms, $R_3$ stands for hydrogen, halogen, an alkyl group having 1 to 4 carbon atoms, an alkoxy group or a dialkylamino group having 1 to 4 carbon atoms, n stands for an integer of 1 or 2 and in case n is 2 $R_3$ may be the same or different and $R_4$ and $R_5$ stand for hydrogen, and a substituted or unsubstituted alkyl or benzyl group.)

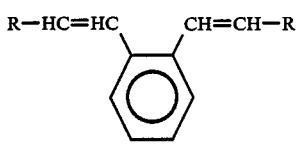
(7)

(wherein, R stands for a carbazolyl group, a pyridyl group, a thienyl group, an indolyl group, a furyl group or each substituted or unsubstituted phenyl group, styryl group, naphthyl group or anthryl group, each substituent being one member selected from the group consisting of a dialkylamino group, an alkyl group, an alkoxy group, a carboxy group or their esters, a halogen atom, a cyano group, an aralkyl amino group, an N-alkyl-N aralkyl amino group, an amino group, a nitro group and an acetylamino group.)

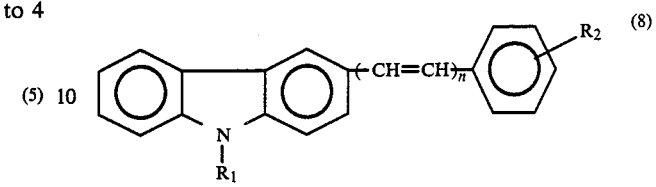
(8)

(wherein, $R_1$ stands for a lower alkyl group or a benzyl group, $R_2$ stands for a hydrogen atom, a lower alkyl group, a lower alkoxy group, a halogen atom, a nitro group, an amino group or a lower alkyl group or a benzyl substituted amino group, and n is an integer of 1 or 2.)

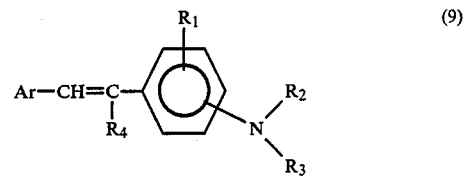
(9)

(wherein, $R_1$ stands for a hydrogen atom, an alkyl group, an alkoxy group or a halogen atom, $R_2$ and $R_3$ each stands for an alkyl group, a substituted or unsubstituted aralkyl group or a substituted or unsubstituted aryl group, $R_4$ stands for a hydrogen atom or a substituted or unsubstituted phenyl group, and Ar stands for a phenyl group or a naphthyl group.)

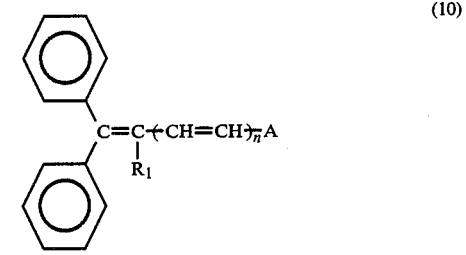
(10)

[wherein, n stands for an integer of 0 or 1, $R_1$ stands for a hydrogen atom, an alkyl group or a substituted or unsubstituted phenyl group, A stands for

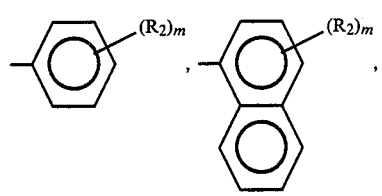

9-anthryl group or a substituted or unsubstituted N-alkyl-carbazolyl group, $R_2$ stands for a hydrogen atom, an alkyl group, an alkoxy group, a halogen atom or

(wherein, R₃ and R₄ each stands for an alkyl group, a substituted or unsubstituted aralkyl group, a substituted or unsubstituted aryl group, and R₃ and R₄ may form a ring), m stands for an integer of 0, 1, 2 or 3, and in case m is more than 2 R₂ may be the same or different.]

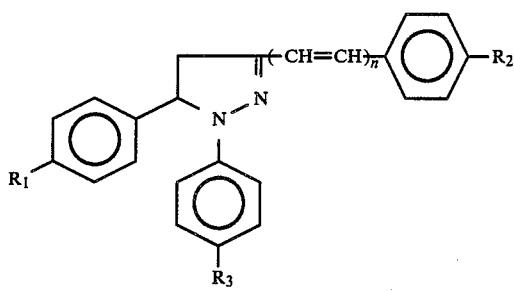

(wherein, R₁, R₂ and R₃ each stands for hydrogen, a lower alkyl group, a lower alkoxy group, a dialkylamino group or a halogen atom, and n stands for an integer of 0 or 1.)

The compounds represented by the general formula (I) include for instance 9-ethylcarbazole-3-aldehyde-1-methyl-1-phenyl-hydrazone, 9-ethylcarbazole-3-aldehyde-1-benzyl-1-phenylhydrazone, 9-ethylcarbazole-3-aldehyde-1,1-diphenylhydrazone and the like. The compounds represented by the general formula (2) include for instance 4-diethylaminostyrene-β-aldehyde-1-methyl-1-phenylhydrazone, 4-methoxynaphthalene-1-aldehyde-1-benzyl-1-phenylhydrazone and the like. The compounds represented by the general formula (3) include for instance 4-methoxybenzaldehyde-1-methyl-1-phenylhydrazone, 2,4-dimethoxybenzaldehyde-1-benzyl-1-phenylhydrazone, 4-diethylaminobenzaldehyde-1,1-diphenylhydrazone, 4-methoxybenzaldehyde-1-benzyl-1-(4-methoxy)phenylhydrazone, 4-diphenylaminobenzaldehyde-1-benzyl-1-phenyl-hydrazone, 4-dibenzylaminobenzaldehyde-1,1-diphenylhydrazone and the like. The compounds represented by the general formula (4) include for instance 1,1-bis(4-dibenzylaminophenyl)propane, tris(4-diethyl-aminophenyl)methane, 1,1-bis(4-dibenzylaminophenyl)propane, 2,2'-dimethyl-4,4'-bis(diethylamino)-triphenylmethane and the like. The compounds represented by the general formula (5) include for instance 9-(4-diethylaminostyryl)anthracene, 9-bromo-10-(4-diethylaminostyryl)anthracene and the like. The compounds represented by the general formula (6) include for instance 9-(4-dimethylaminobenzylidene)fluorene, 3-(9-fluorenylidene)-9-ethylcarbazole and the like. The compounds represented by the general formula (7) include for instance 1,2-bis(4-diethylaminostyryl)benzene, 1,2-bis(2,4-dimethoxystyryl)benzene and the like. The compounds represented by the general formula (8) include for instance 3-styryl-9-ethylcarbazole, 3-(4-methoxystyryl)-9-ethylcarbazole and the like. The compounds represented by the general formula (9) include for instance 4-diphenylaminostilbene, 4-dibenzylaminostilbene, 4-ditolylaminostilbene, 1-(4-diphenylaminostyryl)naphthalene, 1-(4-diethylaminostyryl)naphthalene and the like. The compounds represented by the general formula (10) include for instance 4'-diphenylamino-α-phenylstilbene, 4'-methylphenylamino-α-phenylstilbene and the like. The compounds represented by the general formula (11) include for instance 1-phenyl-3-(4-diethylaminostyryl)-5-(4-diethylaminophenyl)pyrazoline, 1-phenyl-3-(4-dimethylaminostyryl)-5-(4-dimethylaminophenyl)pyrazoline and the like.

As the other hole transfer materials, there can be used the following low molecular compounds and high molecular compounds. The former includes for instance oxadiazole compounds such as 2,5-bis(4-diethylaminophenyl)-1,3,4-oxadiazole, 2,5-bis[4-(4-diethylaminostyryl)phenyl]-1,3,4-oxadiazole, 2-(9-ethylcarbazolyl-3-)-5-(4-diethylaminophenyl)-1,3,4-oxadiazole and the like, oxazole compounds such as 2-vinyl-4-(2-chlorophenyl)-5-(4-diethylaminophenyl)oxazole, 2-(4-diethylaminophenyl)-4-phenyl oxazole and the like. The latter includes poly-N-vinylcarbazole, halogenated poly-N-vinylcarbazole, polyvinyl pyrene, polyvinyl anthracene, pyreneformaldehyde resin, ethylcarbazole formaldehyde resin and the like.

As the electron transfer materials there may be enumerated for instance chloranil, bromanil, tetracyanoethylene, tetracyanoquinone dimethane, 2,4,7-trinitro-9-fluorenone, 2,4,5,7-tetranitro-9-fluorenone, 2,4,5,7-tetranitroxanthone, 2,4,8-trinitroxanthone, 2,6,8-trinitro-4H-indeno[1,2-b]thiophene-4-one, 1,3,7-trinitrodibenzothiophene-5,5-dioxide and the like.

These charge transfer materials may be used singly or in combination of two or more materials.

In the case of the thus obtained electrophotographic element, it is possible to dispose an adhesion layer or a barrier layer between the electrically conductive substrate and the photo-sensitive layer as occasion demands. The materials used suitably in these layers are polyamide, nitrocellulose, aluminum oxide and the like; and the film thickness is preferable to be 1μ or less.

The electrophotographic element shown in FIG. 3 may be prepared by the steps of vapor-depositing a disazo compound on the electrically conductive substrate by means of the vacuum vapordeposition method disclosed in U.S. Pat. No. 3,973,959, U.S. Pat. No. 3,996,049 or the like, or coating the surface of the electrically conductive substrate with a suitable dispersion obtained by dispersing fine disazo compound particles in a proper solvent dissolved, if necessary, a binder therein and drying, and further surface-finishing, if more needed, by buffing as shown, for instance, in Japanese Laid Open Patent Application No. 90827/1976 or adjusting the film thickness, and thereafter coating and drying the thus treated surface with the solution containing the charge transfer material and the binder.

The electrophotographic element shown in FIG. 4 may be prepared by dispersing disazo compound particles in the solution obtained by dissolving the charge transfer material and the binder, and coating and drying the surface of the electrically conductive substrate with this solution. In each case, the disazo compound used in the present invention is pulverized into particles whose diameter is 5μ or less, preferably 2μ or less, by means of a ball mill or the like. The coating operation is effected in a normal manner such, for instance, as a doctor blade, dipping, a wire bar or the like.

The copying operation using the electrophotographic element of the present invention can be achieved by subjecting the surface of the photosensitive layer to electrification and exposure and thereafter developing, and, if needed, transferring the developed image to paper or the like.

As is evident from the above explanation and examples and comparative examples referred to afterwards, the electrophotographic element according to the present invention displays superior characteristics, as compared with the conventional elements, by using the disago compound having the xanthone skeleton as the charge carrier generating material, in particular that the electrophotographic element of the present invention is easy to manufacture, is of high sensitivity, has the sensitive wavelength range localized within the short wavelength range (450-600 nm), is of stable characteristics even when used repeatedly and the like.

Figure 1:
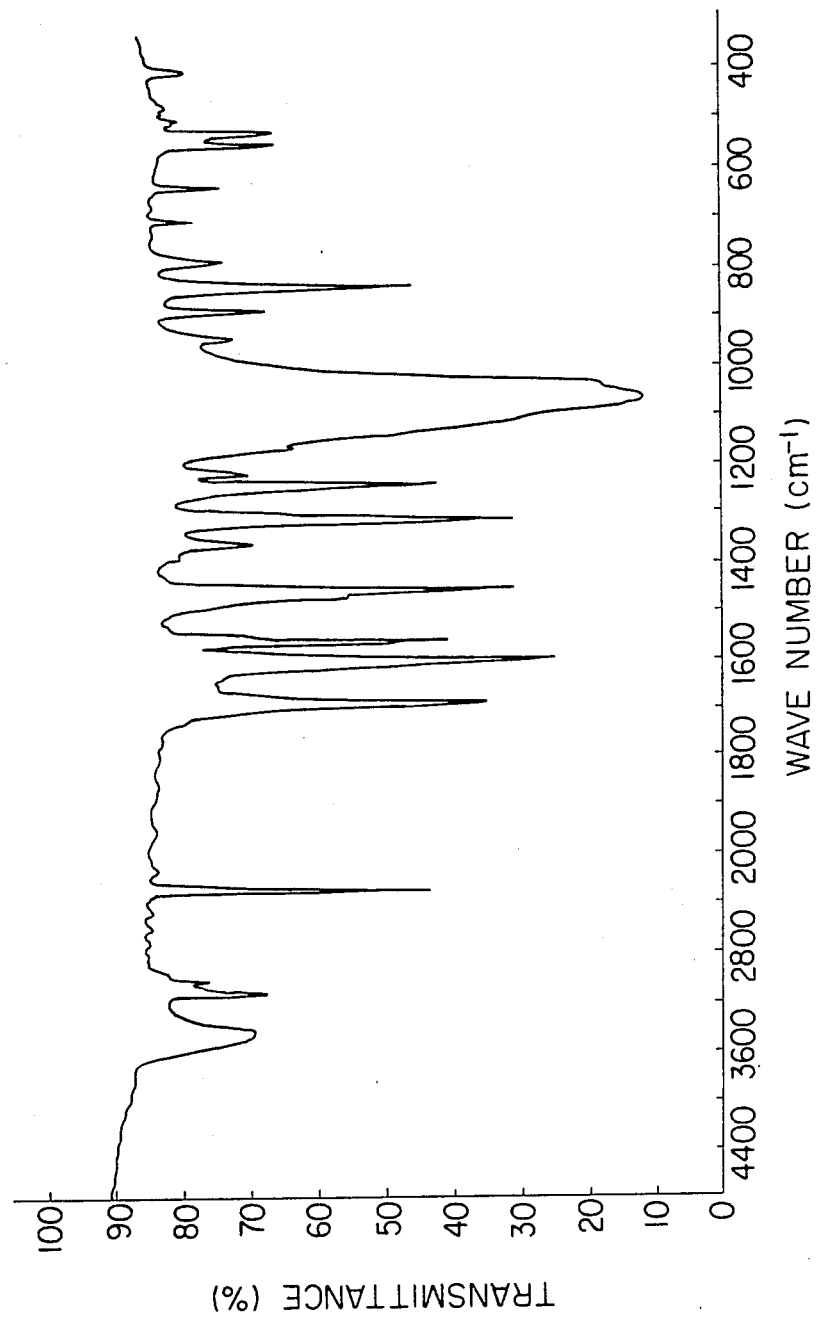
FIG. 1 is a view illustrating infrared absorption spectrums (KBr tablet method) of the tetrazonium salt compound prepared according to Example 1.

The reference numerals in the drawings identify elements as follows:

11 ... electrically conductive substrate
13 ... disazo compound
15 ... charge carrier generating layer
17 ... charge transfer layer
19,19' ... photosensitive layer

PREFERRED EMBODIMENTS OF THE INVENTION

Next, the present invention will be explained concretely with reference to Examples, but the present invention should not be limited thereto.

EXAMPLE 1

(Preparation of the tetrazonium salt)

29.18 g of 2,7-diaminoxanthone was added to a diluted hydrochloric acid comprising 224 ml of water and 224 ml of concentrated hydrochloric aicd. This maxture was heated at about 60° C. for 1 hour and then cooled to $-3°$ C. In succession, a solution obtained by dissolving 18.7 g of sodium nitrite in 90 ml of water was dropped in the thus treated mixture at a temperature of $-3°$ C. to 0° C. for 50 minutes. Thereafter, the same was stirred at the same temperature for 30 minutes, and then 150 ml of 42% borofluoric acid was added to this reaction solution. Separated crystals were filtrated, washed with water and dried to thereby obtain 47.13 g (yield: 86.1%) of pale yellow crystals of tetrazonium fluoroborate. This compound was observed to have a decomposition point of 145° C. or more, show the infrared absorption spectrum (KBr tablet method) as illustrated in FIG. 1, and have an absorption band caused by $N_2^\oplus$ at 2280 cm$^{-1}$ and an absorption band caused by $>C=0$ at 1685 cm$^{-1}$.

EXAMPLE 2

[Preparation of the disazo compound according to the formula (II)]

50 g of the tetrazonium salt obtained according to Example 1 and 6.25 g of 2-hydroxy-3-naphthoic acid anilide (whose moles are twice as large as those of tetrazonium salt) which acts as a coupler, were dissolved in 700 ml of cooled N,N-dimethyl formamide. A solution comprising 4.0 g of sodium acetate and 35 ml of water was dropped therein at a temperature of 5° to 10° C. for 20 minutes, and after the stop of cooling, the mixture was further stirred at room temperature for 3 hours. Subsequently, the formed precipitates were filtered out, washed 3 times with 700 ml of N,N-dimethyl formamide heated to 80° C., next washed 2 times with 700 ml of water, and dried at 80° C. at a reduced pressure of 2 mmHg to obtain 8.2 g (yield 90.0%) of No. 1 disazo compound. This disazo compound looks like a red powder externally.

Figure 2:
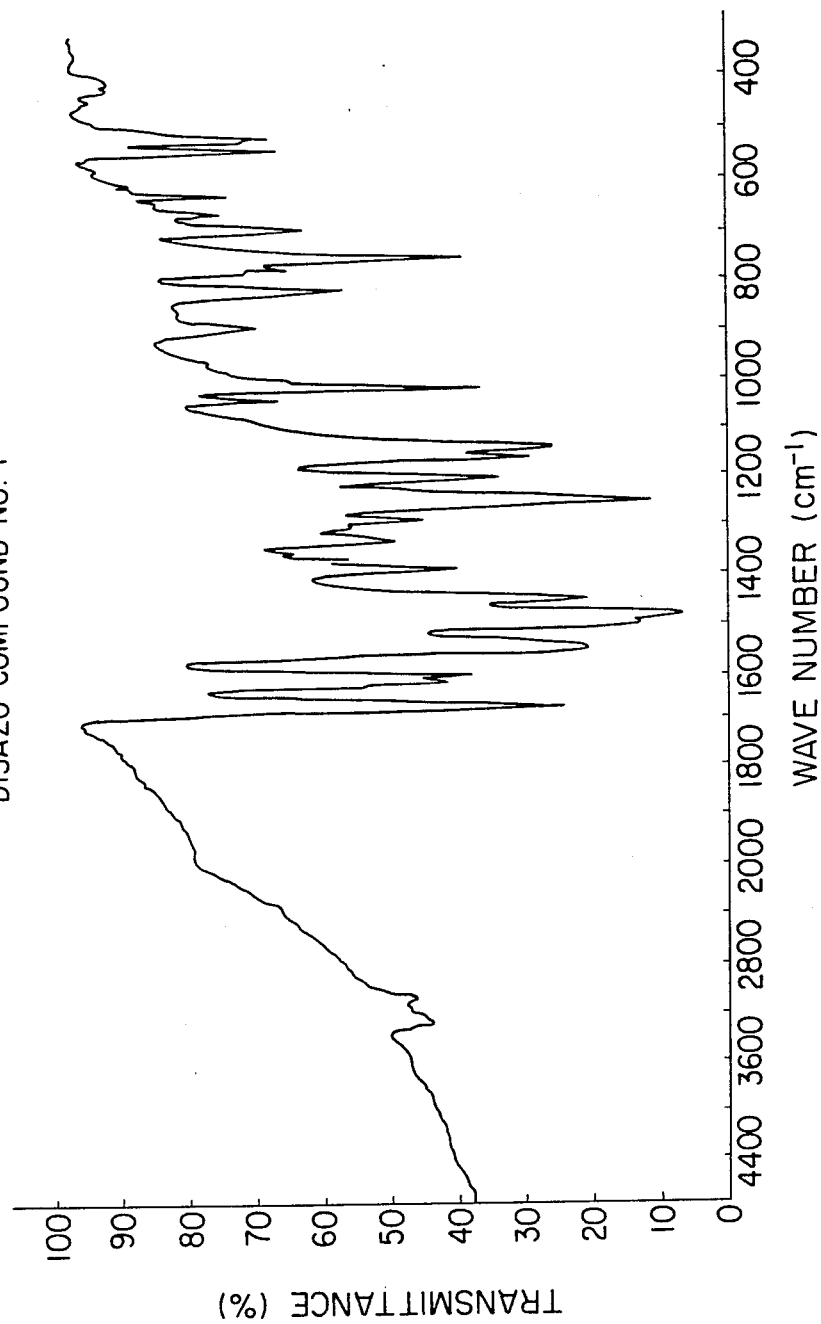
FIG. 2 is a view illustrating infrared absorption spectrums (KBr tablet method) of the typical disazo compounds according to the present invention.

Its infrared spectrum (KBr tablet method) was shown in FIG. 2.

EXAMPLE 3 TO EXAMPLE 40

[Preparation of disazo compounds of the formula (II)]

Disazo compounds according to the formula (II) were prepared by repeating the exactly same procedure as Example 1 except that the following compounds shown in Table 1 were used as couplers.

TABLE 1

| Example No. | Compound No. | Coupler | Yield (%) (appearance) |
|---|---|---|---|
| 3 | 2 | HO-[naphthalene]-CONH-[phenyl-CH₃] | 87.6 (red) |

TABLE 1-continued
| Example No. | Compound No. | Coupler | Yield (%) (appearance) |
|---|---|---|---|
| 4 | 3 | 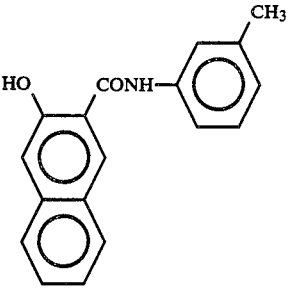 | 93.4 (red) |
| 5 | 4 | 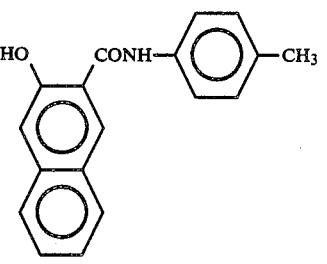 | 84.4 (red) |
| 6 | 8 | 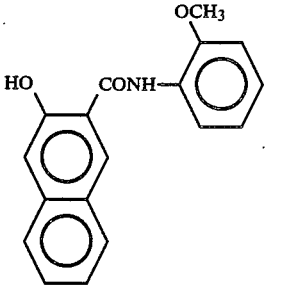 | 88.3 (red) |
| 7 | 9 | 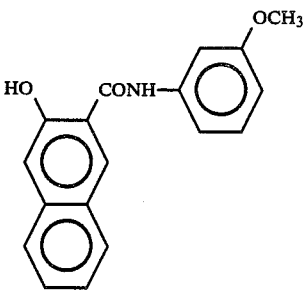 | 67.5 (red) |
| 8 | 10 | 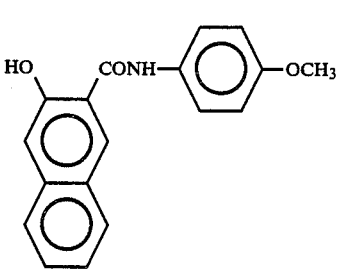 | 74.6 (red) |

TABLE 1-continued

| Example No. | Compound No. | Coupler | Yield (%) (appearance) |
|---|---|---|---|
| 9 | 5 | 3-hydroxy-2-naphthoyl-(2-ethyl)anilide | 81.6 (red) |
| 10 | 7 | 3-hydroxy-2-naphthoyl-(4-ethyl)anilide | 83.1 (red) |
| 11 | 11 | 3-hydroxy-2-naphthoyl-(2-ethoxy)anilide | 91.4 (red) |
| 12 | 12 | 3-hydroxy-2-naphthoyl-(3-ethoxy)anilide | 91.8 (red) |
| 13 | 13 | 3-hydroxy-2-naphthoyl-(4-ethoxy)anilide | 76.1 (red) |

TABLE 1-continued

| Example No. | Compound No. | Coupler | Yield (%) (appearance) |
|---|---|---|---|
| 14 | 14 | 3-hydroxy-2-naphthoic acid 2-chloroanilide | 83.4 (red) |
| 15 | 15 | 3-hydroxy-2-naphthoic acid 3-chloroanilide | 81.9 (red) |
| 16 | 16 | 3-hydroxy-2-naphthoic acid 4-chloroanilide | 86.4 (red) |
| 17 | 17 | 3-hydroxy-2-naphthoic acid 2-bromoanilide | 78.6 (red) |
| 18 | 18 | 3-hydroxy-2-naphthoic acid 3-bromoanilide | 85.4 (red) |

TABLE 1-continued
| Example No. | Compound No. | Coupler | Yield (%) (appearance) |
|---|---|---|---|
| 19 | 19 | 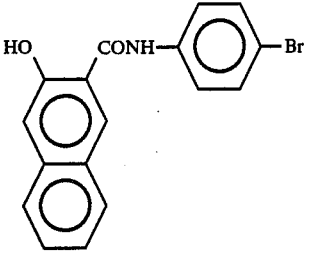 | 84.0 (red) |
| 20 | 20 | 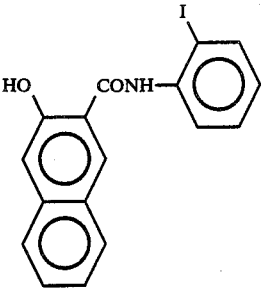 | 83.2 (red) |
| 21 | 21 | 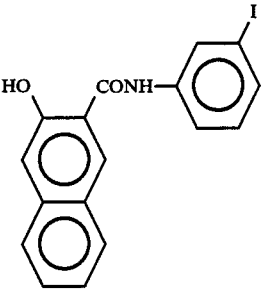 | 85.5 (red) |
| 22 | 23 | 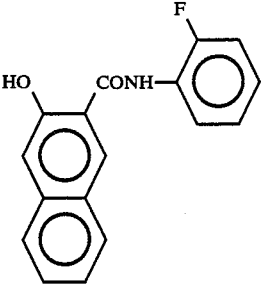 | 81.5 (red) |
| 23 | 25 | 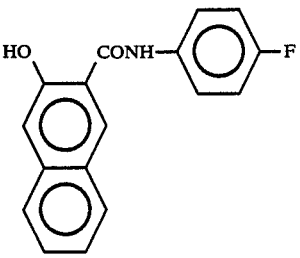 | 78.1 (red) |

TABLE 1-continued
| Example No. | Compound No. | Coupler | Yield (%) (appearance) |
|---|---|---|---|
| 24 | 29 | 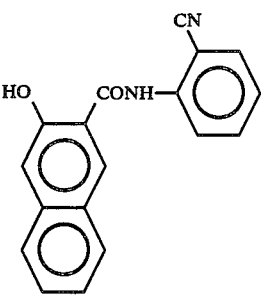 | 82.5 (red) |
| 25 | 26 | 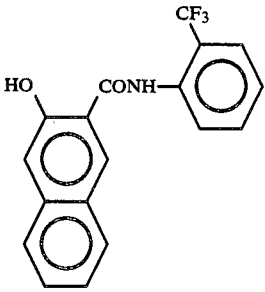 | 86.3 (red) |
| 26 | 32 | 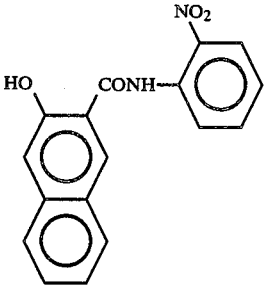 | 78.9 (red) |
| 27 | 33 | 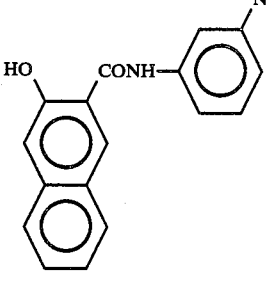 | 85.3 (red) |
| 28 | 34 | 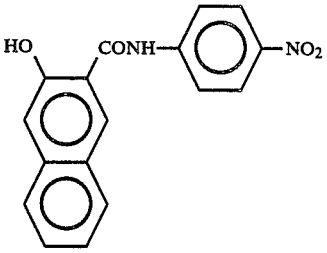 | 75.5 (red) |

TABLE 1-continued

| Example No. | Compound No. | Coupler | Yield (%) (appearance) |
|---|---|---|---|
| 29 | 44 | 3-hydroxy-2-naphthoyl-(2,4-dimethyl)anilide | 90.1 (red) |
| 30 | 41 | 3-hydroxy-2-naphthoyl-(2,5-dichloro)anilide | 82.3 (red) |
| 31 | 45 | 3-hydroxy-2-naphthoyl-(2-methyl-4-chloro)anilide | 80.0 (red) |
| 32 | 77 | 3-hydroxy-2-naphthoyl benzylidenehydrazide | 92.0 (red) |
| 33 | 58 | (HO)(CONH-phenyl) naphthalene fused with indole (HN) | 82.0 (dark red) |

TABLE 1-continued
| Example No. | Compound No. | Coupler | Yield (%) (appearance) |
|---|---|---|---|
| 34 | 90 | 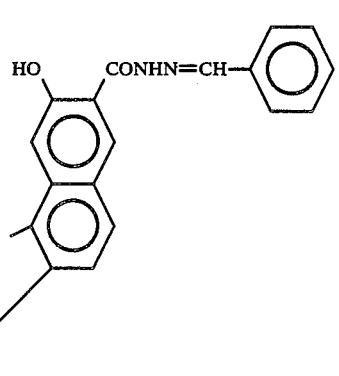 | 65.1 (dark red) |
| 35 | 84 | 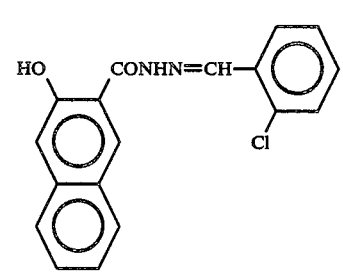 | 85.0 (red) |
| 36 | 163 | 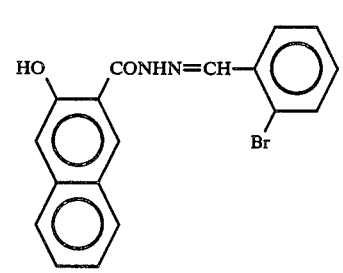 | 71.3 (red) |
| 37 | 61 | 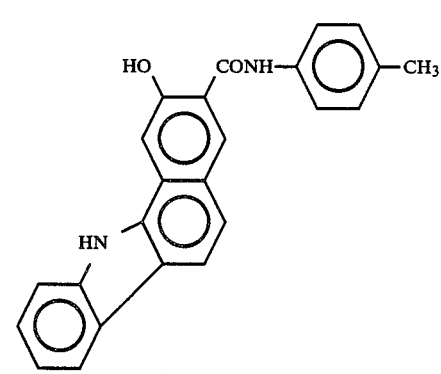 | 83.1 (dark red) |

TABLE 1-continued

| Example No. | Compound No. | Coupler | Yield (%) (appearance) |
|---|---|---|---|
| 38 | 65 | 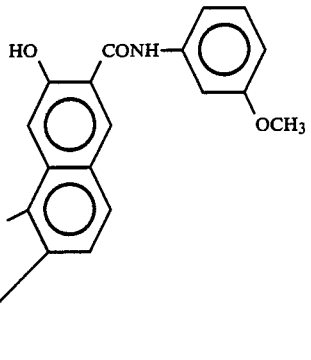 | 74.5 (dark red) |
| 39 | 86 | 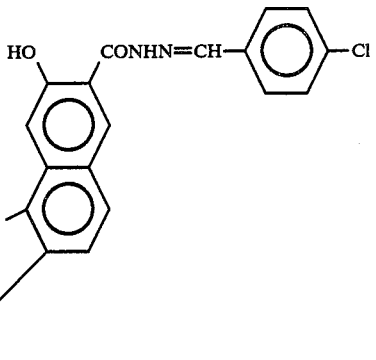 | 78.0 (dark red) |
| 40 | 164 | 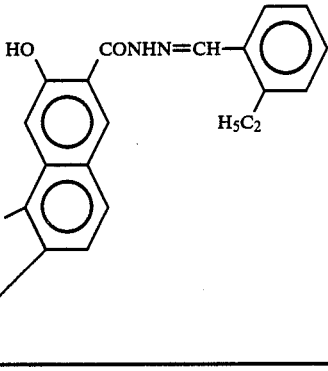 | 71.1 (dark red) |

And, the data such as melting points, elementary analysis values and infrared absorption spectrums of the thus obtained disazo compounds were shown in the following Table-2.

TABLE 2

| Example No. | Compound No. | Melting Point | Element | Elementary Analysis Value Calculated value (%) | Measured Value (%) | IR Absorption Spectrum (KBr disc)$\nu c = 0 (cm^{-1})$ |
|---|---|---|---|---|---|---|
| 2 | 1 | 300° C. or more | C<br>H<br>N | 72.86<br>3.91<br>10.84 | 72.61<br>3.88<br>10.77 | 1675 |
| 3 | 2 | 300° C. or more | C<br>H<br>N | 73.30<br>4.28<br>10.46 | 73.12<br>4.27<br>10.44 | 1675 |
| 4 | 3 | 300° C. or more | C<br>H<br>N | 73.30<br>4.28<br>10.46 | 73.04<br>4.30<br>10.46 | 1670 |
| 5 | 4 | 300° C. or more | C<br>H<br>N | 73.30<br>4.28<br>10.46 | 73.41<br>4.25<br>10.46 | 1665 |

TABLE 2-continued

| Example No. | Compound No. | Melting Point | Element | Elementary Analysis Value Calculated value (%) | Measured Value (%) | IR Absorption Spectrum (KBr disc)$\nu c = 0 (cm^{-1})$ |
|---|---|---|---|---|---|---|
| 6 | 8 | 300° C. or more | C | 70.49 | 70.25 | 1670 |
|   |   |   | H | 4.11 | 4.02 |   |
|   |   |   | N | 10.06 | 9.97 |   |
| 7 | 9 | 300° C. or more | C | 70.49 | 70.21 | 1675 |
|   |   |   | H | 4.11 | 4.07 |   |
|   |   |   | N | 10.06 | 9.97 |   |
| 8 | 10 | 300° C. or more | C | 70.49 | 70.28 | 1670 |
|   |   |   | H | 4.11 | 4.01 |   |
|   |   |   | N | 10.06 | 9.99 |   |
| 9 | 5 | 300° C. or more | C | 73.72 | 73.67 | 1670 |
|   |   |   | H | 4.62 | 4.55 |   |
|   |   |   | N | 9.99 | 10.09 |   |
| 10 | 7 | 300° C. or more | C | 73.72 | 73.58 | 1670 |
|   |   |   | H | 4.62 | 4.53 |   |
|   |   |   | N | 9.99 | 10.10 |   |
| 11 | 11 | 300° C. or more | C | 70.98 | 71.02 | 1665 |
|   |   |   | H | 4.45 | 4.34 |   |
|   |   |   | N | 9.73 | 9.82 |   |
| 12 | 12 | 300° C. or more | C | 70.98 | 70.91 | 1670 |
|   |   |   | H | 4.45 | 4.32 |   |
|   |   |   | N | 9.73 | 9.71 |   |
| 13 | 13 | 300° C. or more | C | 70.98 | 70.74 | 1665 |
|   |   |   | H | 4.45 | 4.33 |   |
|   |   |   | N | 9.73 | 9.60 |   |
| 14 | 14 | 300° C. or more | C | 66.91 | 66.89 | 1675 |
|   |   |   | H | 3.35 | 3.43 |   |
|   |   |   | N | 9.96 | 9.92 |   |
| 15 | 15 | 300° C. or more | C | 66.91 | 66.70 | 1670 |
|   |   |   | H | 3.35 | 3.29 |   |
|   |   |   | N | 9.96 | 9.90 |   |
| 16 | 16 | 300° C. or more | C | 66.91 | 66.83 | 1675 |
|   |   |   | H | 3.35 | 3.42 |   |
|   |   |   | N | 9.96 | 10.08 |   |
| 17 | 17 | 300° C. or more | C | 60.53 | 60.27 | 1675 |
|   |   |   | H | 3.03 | 2.84 |   |
|   |   |   | N | 9.01 | 8.91 |   |
| 18 | 18 | 300° C. or more | C | 60.53 | 60.43 | 1670 |
|   |   |   | H | 3.03 | 2.80 |   |
|   |   |   | N | 9.01 | 8.96 |   |
| 19 | 19 | 300° C. or more | C | 60.53 | 60.30 | 1670 |
|   |   |   | H | 3.03 | 2.81 |   |
|   |   |   | N | 9.01 | 9.10 |   |
| 20 | 20 | 300° C. or more | C | 54.99 | 54.72 | 1675 |
|   |   |   | H | 2.75 | 2.62 |   |
|   |   |   | N | 8.18 | 8.01 |   |
| 21 | 21 | 300° C. or more | C | 54.99 | 54.79 | 1670 |
|   |   |   | H | 2.75 | 2.70 |   |
|   |   |   | N | 8.18 | 8.15 |   |
| 22 | 23 | 300° C. or more | C | 69.62 | 69.58 | 1675 |
|   |   |   | H | 3.49 | 3.39 |   |
|   |   |   | N | 10.36 | 10.30 |   |
| 23 | 25 | 300° C. or more | C | 69.62 | 69.47 | 1670 |
|   |   |   | H | 3.49 | 3.43 |   |
|   |   |   | N | 10.36 | 10.31 |   |
| 24 | 29 | 300° C. or more | C | 71.35 | 71.19 | 1675 |
|   |   |   | H | 3.43 | 3.40 |   |
|   |   |   | N | 13.58 | 13.48 |   |
| 25 | 26 | 300° C. or more | C | 64.61 | 64.51 | 1675 |
|   |   |   | H | 3.11 | 3.10 |   |
|   |   |   | N | 9.22 | 9.18 |   |
| 26 | 32 | 300° C. or more | C | 65.28 | 65.28 | 1680 |
|   |   |   | H | 3.27 | 3.09 |   |
|   |   |   | N | 12.95 | 12.75 |   |
| 27 | 33 | 300° C. or more | C | 65.28 | 65.01 | 1675 |
|   |   |   | H | 3.27 | 3.31 |   |
|   |   |   | N | 12.95 | 12.82 |   |
| 28 | 34 | 300° C. or more | C | 65.28 | 65.08 | 1680 |
|   |   |   | H | 3.27 | 3.09 |   |
|   |   |   | N | 12.95 | 12.71 |   |
| 29 | 44 | 300° C. or more | C | 73.72 | 73.68 | 1670 |
|   |   |   | H | 4.62 | 4.59 |   |
|   |   |   | N | 10.11 | 10.10 |   |
| 30 | 41 | 300° C. or more | C | 61.86 | 61.75 | 1675 |
|   |   |   | H | 2.88 | 2.83 |   |
|   |   |   | N | 9.21 | 9.11 |   |
| 31 | 45 | 300° C. or more | C | 67.51 | 67.44 | 1675 |
|   |   |   | H | 3.71 | 3.75 |   |
|   |   |   | N | 9.64 | 9.62 |   |
| 32 | 77 | 300° C. | C | 71.00 | 70.77 | 1675 |

TABLE 2-continued

| Example No. | Compound No. | Melting Point | Element | Elementary Analysis Value Calculated value (%) | Measured Value (%) | IR Absorption Spectrum (KBr disc)$\nu c = 0(cm^{-1})$ |
| --- | --- | --- | --- | --- | --- | --- |
|  |  | or more | H | 3.90 | 4.00 |  |
|  |  |  | N | 13.51 | 13.64 |  |
| 33 | 58 | 300° C. | C | 74.52 | 74.21 | 1670 |
|  |  | or more | H | 3.61 | 3.48 |  |
|  |  |  | N | 11.78 | 11.61 |  |
| 34 | 90 | 300° C. | C | 72.90 | 72.65 | 1665 |
|  |  | or more | H | 3.48 | 3.48 |  |
|  |  |  | N | 13.93 | 13.67 |  |
| 35 | 84 | 300° C. | C | 65.55 | 65.38 | 1665 |
|  |  | or more | H | 3.35 | 3.35 |  |
|  |  |  | N | 12.48 | 12.41 |  |
| 36 | 163 | 300° C. | C | 59.65 | 59.40 | 1665 |
|  |  | or more | H | 3.07 | 3.01 |  |
|  |  |  | N | 11.35 | 11.26 |  |
| 37 | 61 | 300° C. | C | 74.83 | 74.70 | 1675 |
|  |  | or more | H | 3.92 | 3.92 |  |
|  |  |  | N | 11.44 | 11.45 |  |
| 38 | 65 | 300° C. | C | 72.46 | 72.22 | 1675 |
|  |  | or more | H | 3.80 | 3.68 |  |
|  |  |  | N | 11.08 | 11.00 |  |
| 39 | 86 | 300° C. | C | 68.09 | 67.88 | 1670 |
|  |  | or more | H | 3.38 | 3.27 |  |
|  |  |  | N | 13.01 | 13.00 |  |
| 40 | 164 | 300° C. | C | 73.57 | 73.52 | 1670 |
|  |  | or more | H | 4.19 | 4.11 |  |
|  |  |  | N | 13.19 | 13.08 |  |

EXAMPLE 41

(Preparation of an electrophotographic element)

76 parts by weight of disazo compound No. 1, 1260 parts by weight of tetrahydrofuran solution (solid concentration: 2%) of polyester resin (VYLON 200: produced by TOYO BOSEKI K.K.), and 3700 parts by weight of tetrahydrofuran were pulverized and mixed in a ball mill. The thus obtained dispersion was applied onto the aluminum face of an aluminum-vapordeposited polyester base (electrically conductive substrate) by means of a doctor blade, and was air-dried, whereby a charge carrier generating layer having a thickness of about 1 μm was formed.

On this charge carrier generating layer therre was applied a solution obtained by mixing and dissolving 2 parts by weight of 9-ethylcarbazole-3-aldehyde-1-methyl-1-phenylhydrazone (charge transfer material), 2 parts by weight of polycarbonate resin (Panlite K-1300: produced by TEIJIN K.K.) and 16 parts by weight of tetrahydrofuran by means of a doctor blade. The same was air-dried, whereby an about 1 μm-thick charge carrier generating layer was formed.

Figure 3:
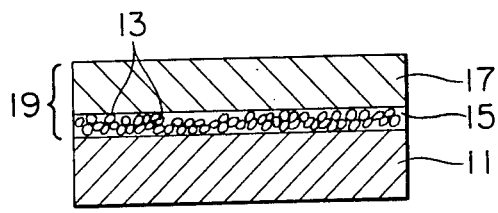
FIG. 3 and FIG. 4 are each an enlarged sectional view illustrating the construction of the element according to the present invention.
Figure 4:
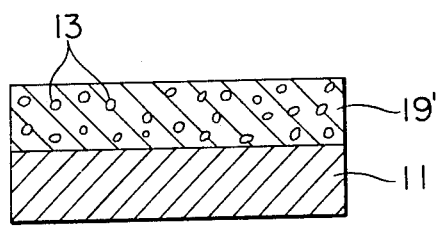

Then, a solution obtained by mixing and dissolving 2 parts by weight of 9-ethylcarbazole-3-aldehyde-1-methyl-1-phenylhydrazone (charge transfer material), 2 parts by weight of polycarbonate resin (Panlite K-1300: produced by TEIJIN K.K.) and 16 parts by weight of tetrahydrofuran was applied on this charge carrier generating layer by means of a doctor blade, was dried at 80° C. for 2 minutes and in succession was dried at 105° C. for 5 minutes, thereby forming an about 20 μm-thick charge transfer layer. Thus, there was prepared a multilayer type electrophotographic element No. 1 shown in FIG. 3.

EXAMPLE 42 TO EXAMPLE 66

Electrophotographic element No. 2 to No. 26 were prepared by repeating the exactly same procedure as Example 41 except that the disazo compound No. 1 used in Example 41 was replaced by the disazo compounds shown in Table-3 referred to afterwards.

EXAMPLE 67 TO EXAMPLE 87

Electrophotographic element No. 27 to No. 47 were prepared by repeating the exactly same procedure as Example 41 except that 1-phenyl-3-(4-diethylaminostyryl)-5-(4-diethylaminophenyl)pyrazoline was used as the charge transfer material and the disazo compounds shown in Table 4 referred to afterwards were used.

EXAMPLE 88 TO EXAMPLE 106

Electrophotographic element No. 48 to No. 66 were prepared by repeating the exactly same procedure as Example 41 except that 9-(4-diethylaminostyryl)anthracene was used as the charge transfer material and the disazo compounds shown in Table-5 referred to afterwards were used.

EXAMPLE 107 TO EXAMPLE 114

Electrophotographic element No. 67 to No. 74 were prepared by repeating the exactly same procedure as Example 41 except that 1,1-bis(4-dibenzylaminophenyl)propane was used as the charge transfer material and the disazo compounds shown in Table-6 referred to afterwards were used.

These electrophotographic elements No. 1 to No. 74 were subjected to −6 KV corona discharge for 20 seconds by means of an electrostatic copying paper tester (SP428 Type: produced by Kawaguchi Electro Works) and charged negatively. Thereafter, these electrophotographic elements were left standing in the dark for 20 seconds to measure the surface potential Vpo(V) at that time. In succession, said elements were exposed to radiation of light from a tungsten lamp so that the intensity of illumination on their surfaces might be 4.5 lux. and, the time (second) required until the surface potential was reduced to ½ of Vpo was found out and the exposure amount E½ (lux.sec) was calculated therefrom on each element. The thus obtained results were shown in Table-3–Table-6.

TABLE 3

| Example No. | Electrophotographic Element No. | Disazo Compound No. | Vpo (volt) | E½ (lux · sec) |
|---|---|---|---|---|
| 41 | 1 | 1 | 1009 | 12.5 |
| 42 | 2 | 2 | 465 | 4.0 |
| 43 | 3 | 8 | 252 | 9.7 |
| 44 | 4 | 14 | 1319 | 2.3 |
| 45 | 5 | 15 | 1260 | 7.9 |
| 46 | 6 | 16 | 852 | 6.2 |
| 47 | 7 | 17 | 1227 | 2.4 |
| 48 | 8 | 18 | 1224 | 4.7 |
| 49 | 9 | 19 | 780 | 8.3 |
| 50 | 10 | 20 | 1211 | 2.7 |
| 51 | 11 | 21 | 1163 | 7.5 |
| 52 | 12 | 22 | 749 | 9.2 |
| 53 | 13 | 23 | 1301 | 3.1 |
| 54 | 14 | 24 | 1215 | 8.5 |
| 55 | 15 | 25 | 830 | 9.0 |
| 56 | 16 | 26 | 1195 | 6.5 |
| 57 | 17 | 27 | 928 | 9.9 |
| 58 | 18 | 29 | 1241 | 8.8 |
| 59 | 19 | 30 | 721 | 12.1 |
| 60 | 20 | 32 | 1270 | 9.9 |
| 61 | 21 | 58 | 738 | 2.0 |
| 62 | 22 | 62 | 922 | 4.8 |
| 63 | 23 | 84 | 1238 | 3.9 |
| 64 | 24 | 85 | 1141 | 8.3 |
| 65 | 25 | 90 | 1140 | 1.3 |
| 66 | 26 | 93 | 1208 | 3.9 |

TABLE 4

| Example No. | Electrophotographic Element No. | Disazo Compound No. | Vpo (volt) | E½ (lux · sec) |
|---|---|---|---|---|
| 67 | 27 | 1 | 1009 | 12.5 |
| 68 | 28 | 2 | 465 | 4.0 |
| 69 | 29 | 3 | 1082 | 13.2 |
| 70 | 30 | 4 | 916 | 8.2 |
| 71 | 31 | 5 | 948 | 15.2 |
| 72 | 32 | 6 | 237 | 5.7 |
| 73 | 33 | 14 | 1123 | 2.2 |
| 74 | 34 | 15 | 1044 | 9.9 |
| 75 | 35 | 17 | 1227 | 2.4 |
| 76 | 36 | 18 | 1045 | 5.5 |
| 77 | 37 | 20 | 1151 | 3.0 |
| 78 | 38 | 21 | 1022 | 8.5 |
| 79 | 39 | 23 | 1198 | 3.3 |
| 80 | 40 | 24 | 995 | 9.1 |
| 81 | 41 | 26 | 1244 | 7.1 |
| 82 | 42 | 29 | 1176 | 7.8 |
| 83 | 43 | 32 | 1235 | 8.2 |
| 84 | 44 | 58 | 208 | 0.8 |
| 85 | 45 | 84 | 1250 | 4.1 |
| 86 | 46 | 87 | 1100 | 10.5 |
| 87 | 47 | 94 | 1095 | 5.5 |

TABLE 5

| Example No. | Electrophotographic Element No. | Disazo Compound No. | Vpo (volt) | E½ (lux · sec) |
|---|---|---|---|---|
| 88 | 48 | 2 | 1436 | 13.9 |
| 89 | 49 | 3 | 1145 | 15.0 |
| 90 | 50 | 4 | 1233 | 19.1 |
| 91 | 51 | 7 | 884 | 13.7 |
| 92 | 52 | 14 | 1240 | 2.9 |
| 93 | 53 | 15 | 1258 | 11.8 |
| 94 | 54 | 16 | 1526 | 10.5 |
| 95 | 55 | 17 | 1121 | 2.9 |
| 96 | 56 | 18 | 1164 | 6.1 |
| 97 | 57 | 19 | 1406 | 18.4 |
| 98 | 58 | 20 | 1310 | 3.5 |
| 99 | 59 | 23 | 1227 | 4.3 |
| 100 | 60 | 32 | 1338 | 18.4 |
| 101 | 61 | 33 | 1085 | 10.9 |
| 102 | 62 | 34 | 1246 | 5.7 |
| 103 | 63 | 58 | 940 | 2.3 |
| 104 | 64 | 84 | 1195 | 3.9 |

TABLE 5-continued

| Example No. | Electrophotographic Element No. | Disazo Compound No. | Vpo (volt) | E½ (lux · sec) |
|---|---|---|---|---|
| 105 | 65 | 89 | 1160 | 7.7 |
| 106 | 66 | 90 | 1164 | 1.6 |

TABLE 6

| Example No. | Electrophotographic Element No. | Disazo Compound No. | Vpo (volt) | E½ (lux · sec) |
|---|---|---|---|---|
| 107 | 67 | 14 | 1514 | 2.6 |
| 108 | 68 | 15 | 1448 | 8.1 |
| 109 | 69 | 17 | 1557 | 2.4 |
| 110 | 70 | 18 | 1557 | 5.4 |
| 111 | 71 | 34 | 1535 | 9.9 |
| 112 | 72 | 58 | 1165 | 3.8 |
| 113 | 73 | 84 | 1410 | 6.7 |
| 114 | 74 | 90 | 1502 | 2.5 |

COMPARATIVE EXAMPLE 1

The multilayer type electrophotographic element disclosed in U.S. Pat. No. 3,871,882, wherein a perylene derivative was incorporated in the charge carrier generating layer and an oxadiazole derivative was incorporated in the charge transfer layer, was prepared in the undermentioned manner.

The charge carrier generating layer was prepared by vacuum vapordepositing N,N'-dimethylperylene-3,4,9,10-tetracarboxylic acid diimide (charge carrier generating material) on an aluminum plate under the conditions: degree of vacuum $10^{-5}$ mmHg; vapordeposition source temperature 350° C., and vapordeposition time 3 minutes. In succession, a solution comprising 5 parts by weight of 2,5-bis(4-diethylaminophenyl)-1,3,4-oxadiazole, 5 parts by weight of polyester resin (Polyester Adhesive 49000, produced by Du Pont Co.) and 90 parts by weight of tetrahydrofuran was applied on this charge carrier generating layer, and dried at 120° C. for 10 minutes, whereby the charge transfer layer having a thickness of about 10 μm was formed. Thus, there was prepared comparative Electrophotographic Element No. 1.

COMPARATIVE EXAMPLE 2

The multilayer type electrophotographic element disclosed in Japanese Patent Publication No. 42380/1980, wherein Chloro Dian Blue was incorporated in the charge carrier generating layer and a hydrazone compound was incorporated in the charge transfer layer, was prepared in the undermentioned manner.

A solution comprising 25 parts by weight of Chloro Dian Blue, 1240 parts by weight of ethylene diamine, 990 parts by weight of n-butylamine and 2740 parts by weight of tetrahydrofuran was applied on the aluminum face of an aluminum-vapordeposited polyester base with a 25μ wet gap by means of a doctor blade and dried, whereby the charge carrier generating layer was prepared. In succession, a solution comprising 10 parts by weight of 4-diethylaminobenzaldehyde-1,1-diphenylhydrazone, 10 parts by weight of polycarbonate resin (the same as that employed in Example 40) and 80 parts by weight of tetrahydrofuran was applied on the thus formed charge carrier generating layer by means of a doctor blade and dried to thereby form the charge transfer layer having a thickness of about 18 μm.

Thus, Comparative Electrophotographic Element No. 2 of multilayer type was prepared.

COMPARATIVE EXAMPLE 3

The multilayer type electrophotographic element disclosed in Japanese Laid Open Patent Application No. 84943/1980, wherein a distyrylbenzene type disazo compound was incorporated in the charge carrier generating layer and a hydrazone compound was incorporated in the charge transfer layer, was prepared in the undermentioned manner.

20 parts by weight of 4',4''-bis[2-hydroxy-3-(2,4-dimethylphenylcarbamoyl)-1-naphthylazo]-1,4-distyrylbenzene, 3 parts by weight of polyvinylbutyral (Denka Butyral #4000-1, produced by Tokyo Denki Kagaku K.K.), 7 parts by weight of polymethyl methacrylate (DIANAL BR-80, produced by Mitsubishi Rayon K.K.) and 300 parts by weight of tetrahydrofuran were ball-milled for 3 hours to thereby obtain a dispersion. This dispersion was diluted with 2700 parts by weight of tetrahydrofuran. Thereafter, this dispersion was applied on the aluminum face of an aluminum-vapordeposited polyester base (electrically conductive substrate) by means of a doctor blade and dried to thereby form an about 0.3 μm-thick charge carrier generating layer. In succession, a solution comprising 10 parts by weight of 9-ethylcarbazole-3-aldehyde 1-methyl-1-phenylhydrazone, 10 parts by weight of polycarbonate resin (the same resin as employed in Example 40) and 80 parts by weight of tetrahydrofuran was applied on said charge carrier generating layer by means of a doctor blade and dried to thereby form an about 13 μm-thick charge transfer layer. Thus, Comparative Electrophotographic Element No. 3 of multilayer type was prepared.

For the purpose of measuring the sensitive wavelengths of these Comparative Electrophotographic Elements No. 1 to No. 3 and Electrophotographic Elements No. 4 and No. 7 of the present invention, their spectral sensitivity was measured in accordance with the following measuring procedure.

First, each electrophotographic element was charged by corona discharge in the dark so that the surface potential might become more than $-800$ V, and then subjected to dark decay until the surface potential became $-800$ V. When the surface potential became $-800$ V, the electrophotographic element was exposed to a monochromatic spectrum obtained by means of a monochrometer so that the intensity of illumination on the surface of the electrophotographic element might be 1 μW/cm$^2$, and the time (second) required until the surface potential decayed to $-400$ V was found out, and the half decay exposure amount (μW.sec/cm$^2$) was calculated therefrom. On the other hand, the potential difference to be obtained actually by the exposure was found out by substracting the dark decayed potential portion from the apparent potential difference 400 V obtained by exposure. Then, the light decay speed (Volt·cm$^2$·μW$^{-1}$·sec$^{-1}$) was calculated from the actual potential difference and the abovementioned half decay exposure amount and was named sensitivity. The thus obtained spectral sensitivity was shown in FIGS. 5-7.

Figure 5:
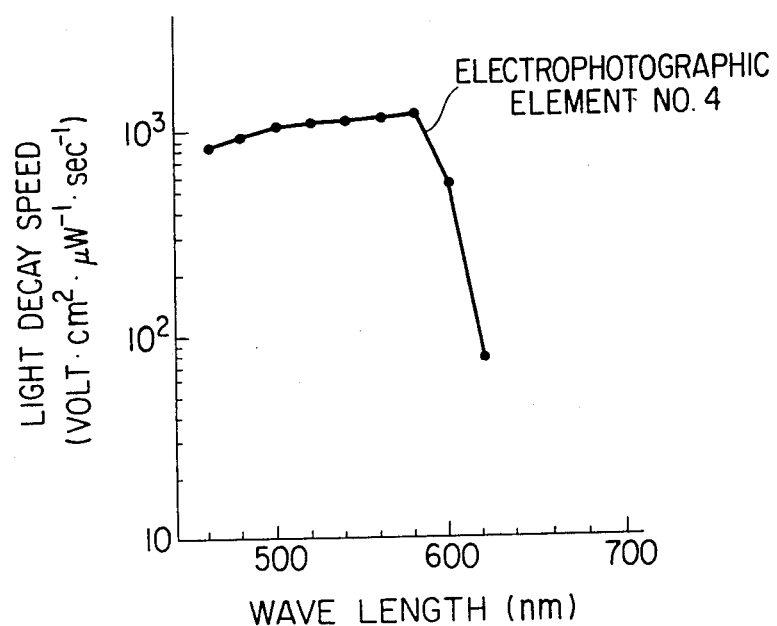
FIG. 5 to FIG. 7 are each a graph illustrating spectral sensitivity characteristics of the element according to the present invention.

FIG. 5 . . . Electrophotographic Element No. 4 of the present invention

Figure 6:
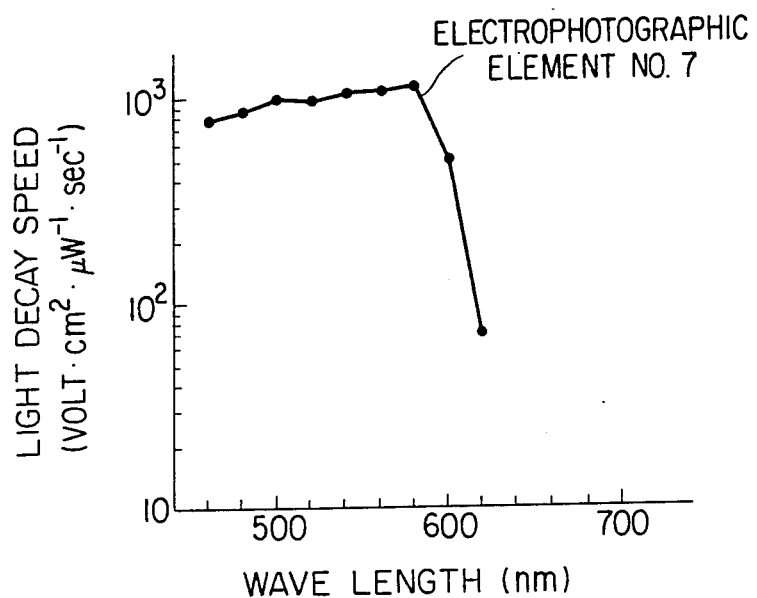

FIG. 6 . . . Electrophotographic Element No. 7 of the present invention

Figure 7:
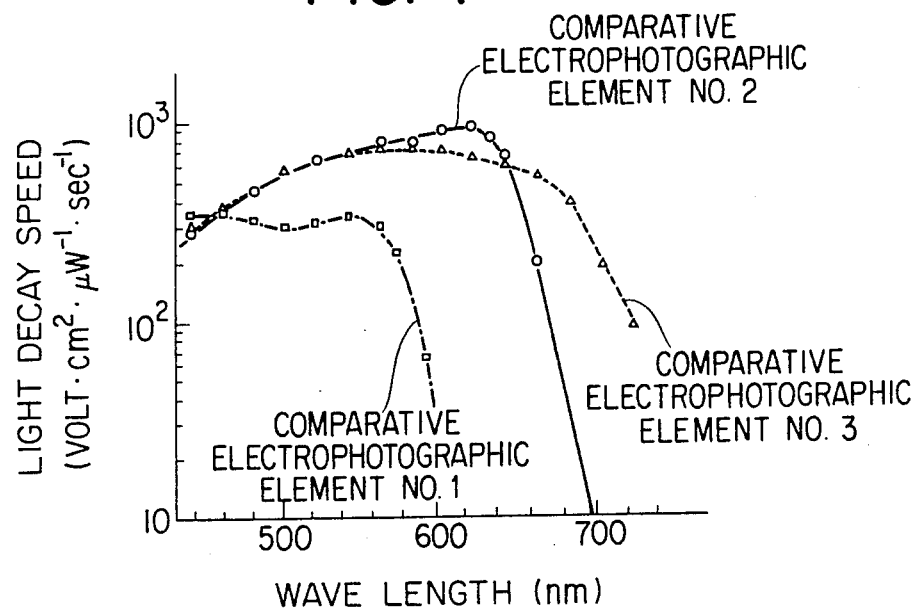

FIG. 7 . . . Electrophotographic Comparative Elements No. 1, No. 2 and No. 3

It can be seen from the above results given in said Table-3 to Table-6 and FIG. 5 to FIG. 7 that the electrophotographic elements according to the present invention are high in sensitivity and their sensitive wavelengths cover about 460 to 600 nm.

Further, Electrophotographic Element No. 4 and No. 7 of the present invention were each subjected to 10,000 time-repeated reproduction by means of a copying machine RICOPY-P-500 manufactured by RICOH COMPANY, LTD.

As the result, each electrophotographic element was found to produce a clear-cut image without any change caused by repetition of copying processes. It may be understood therefrom that the electrophotographic elements of the present invention are also superior in durability.

I claim:

1. A disazo compound represented by the formula

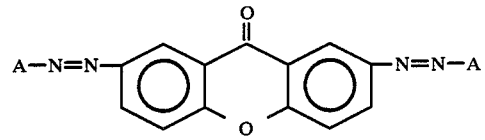

wherein, A stands for

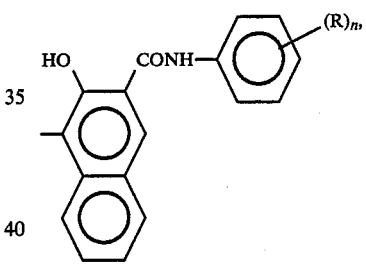

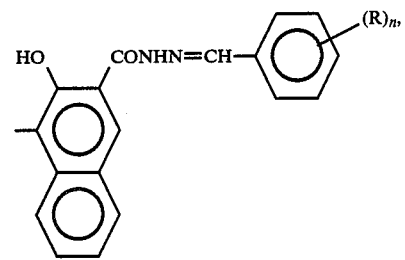

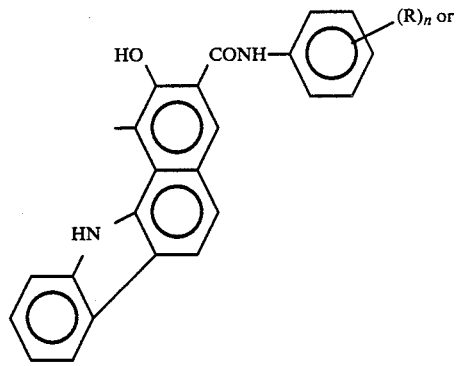

-continued

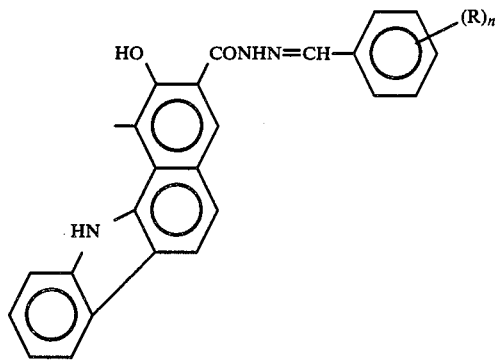

wherein, R stands for alkyl, alkoxy, nitro, halogen, cyano or halomethyl; n stands for an integer of 0, 1, 2 or 3; and in case n is an integer of 2 or 3, each R is the same or different.

2. A disazo compound as claimed in claim 1 in which A is

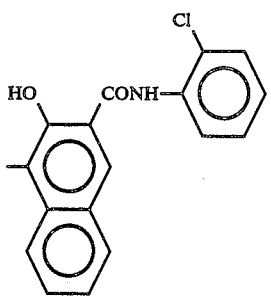

3. A disazo compound as claimed in claim 1 in which A is

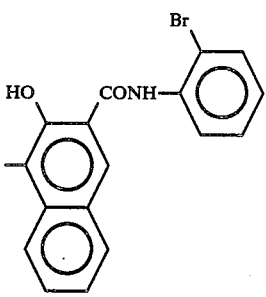

4. A disazo compound as claimed in claim 1 in which A is

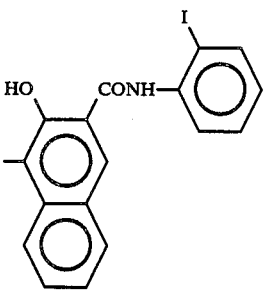

5. A disazo compound as claimed in claim 1 in which A is

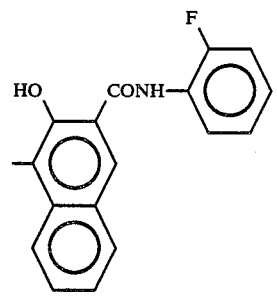

6. A disazo compound as claimed in claim 1 in which A is

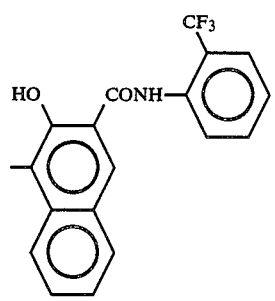

7. A disazo compound as claimed in claim 1 in which A is

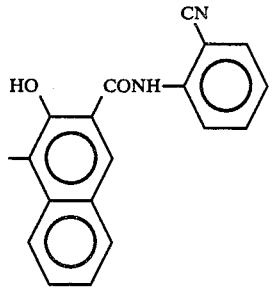

8. A disazo compound as claimed in claim 1 in which A is

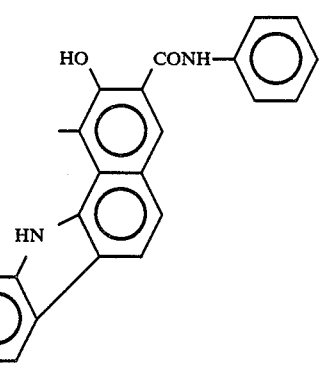

9. A disazo compound as claimed in claim 1 in which A is

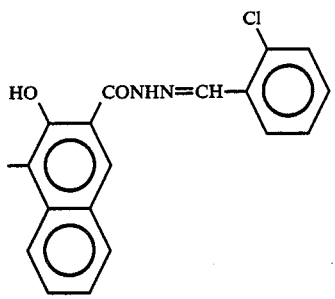

10. A disazo compound as claimed in claim 1 in which A is

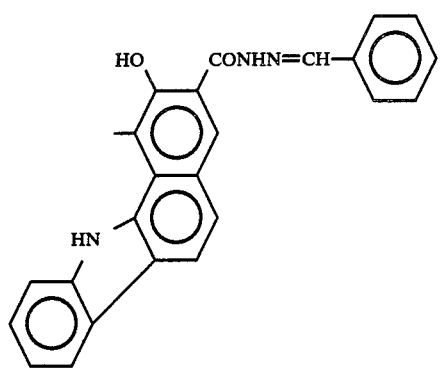

11. A disazo compound as claimed in claim 1 in which R is hydrogen, methyl, ethyl, methoxy, ethoxy, chloro, bromo, iodo, fluoro, trifluoromethyl, cyano or nitro.

12. A disazo compound as claimed in claim 11 in which A is

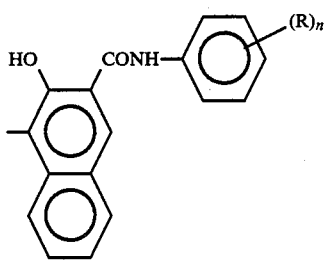

13. A disazo compound as claimed in claim 11 in which A is

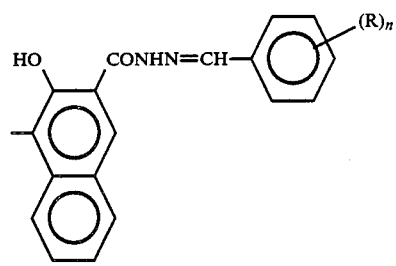

14. A disazo compound as claimed in claim 11 in which A is

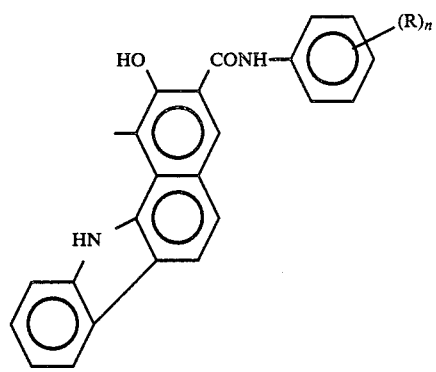

15. A disazo compound as claimed in claim 11 in which A is

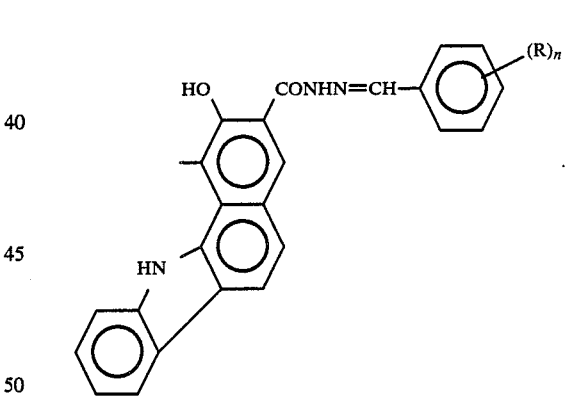

* * * * *